(12) United States Patent
El-Agnaf

(10) Patent No.: US 10,488,417 B2
(45) Date of Patent: Nov. 26, 2019

(54) COMPOUNDS FOR USE AS IMAGING AGENTS

(71) Applicant: United Arab Emirates University, Al Ain (AE)

(72) Inventor: Omar M. Ali El-Agnaf, Morecambe (GB)

(73) Assignee: United Arab Emirates University, Al Ain (AE)

( * ) Notice: Subject to any disclaimer, the term of this patent is extended or adjusted under 35 U.S.C. 154(b) by 184 days.

(21) Appl. No.: 15/526,525

(22) PCT Filed: Nov. 14, 2014

(86) PCT No.: PCT/IB2014/066041
§ 371 (c)(1),
(2) Date: May 12, 2017

(87) PCT Pub. No.: WO2016/075516
PCT Pub. Date: May 19, 2016

(65) Prior Publication Data
US 2017/0307623 A1 Oct. 26, 2017

(51) Int. Cl.
| | |
|---|---|
| *G01N 33/58* | (2006.01) |
| *G01N 33/52* | (2006.01) |
| *G01N 33/68* | (2006.01) |
| *A61K 31/343* | (2006.01) |
| *A61K 31/352* | (2006.01) |
| *A61K 31/704* | (2006.01) |
| *A61K 31/216* | (2006.01) |

(52) U.S. Cl.
CPC ........... *G01N 33/58* (2013.01); *A61K 31/216* (2013.01); *A61K 31/343* (2013.01); *A61K 31/352* (2013.01); *A61K 31/704* (2013.01); *G01N 33/52* (2013.01); *G01N 33/6896* (2013.01); *G01N 2800/28* (2013.01); *G01N 2800/2814* (2013.01); *G01N 2800/2835* (2013.01)

(58) Field of Classification Search
CPC .. A61K 31/216; A61K 31/343; A61K 31/352; A61K 31/704; G01N 2800/28; G01N 2800/2814; G01N 2800/2835; G01N 33/48; G01N 33/52; G01N 33/58; G01N 33/68; G01N 33/6896; Y10T 436/13; Y10T 436/142222; Y10T 436/203332
USPC .................. 436/93, 131, 86, 56, 57, 172
See application file for complete search history.

(56) References Cited

U.S. PATENT DOCUMENTS

| | | | |
|---|---|---|---|
| 2009/0238902 A1* | 9/2009 | Liu ..................... | A61K 9/1652 424/728 |
| 2011/0159527 A1* | 6/2011 | Schlossmacher .. | G01N 33/6896 435/7.92 |
| 2012/0053235 A1 | 3/2012 | Liu et al. | |
| 2012/0251448 A1 | 10/2012 | Hefti et al. | |
| 2014/0241984 A1 | 8/2014 | El-Agnaf | |

FOREIGN PATENT DOCUMENTS

| | | |
|---|---|---|
| CN | 1985836 A | 6/2007 |
| CN | 101239057 A | 8/2008 |
| CN | 102727508 A | 10/2012 |
| CN | 103054847 A | 4/2013 |
| CN | 104116730 A | 10/2014 |
| JP | 2000-191539 A | 7/2000 |
| WO | 99/50300 A1 | 10/1999 |
| WO | 03/069332 A2 | 8/2003 |
| WO | 2009/027690 A1 | 3/2009 |
| WO | 2014/132210 A1 | 9/2014 |

OTHER PUBLICATIONS

Partial Supplementary European Search Report, European Serial No. 14906044.4, dated Jun. 13, 2018, 13 pages.
Van Kampen, Jackalina, M. et al., "Panax Ginseng is Neuroprotective in a Novel Progressive model of Parkinson's Disease." Experimental Gerontology, 50 (2014): 95-105.
Lu, J.-H. et al., "Baicalein inhibits formation of α-synuclein oligomers within living cells and prevents Aβ peptide fibrillation and oligomerisation," ChemBioChem, 2011, vol. 12, pp. 615-624.
Hwang, Y. P. and Jeong, H. G., "Ginsenoside Rb1 protects against 6-hydroxydopamine-induced oxidative stress by increasing heme oxygenase-1 expression through an estrogen receptor-related PI3K/Akt/Nrf2-dependent pathway in human dopaminergic cells," Toxicology and Applied Pharmacology, 2010, vol. 242, pp. 18-28.
Zhou, J. et al., "Salvianolic acid B attenuates toxin-induced neuronal damage via Nrf2-dependent glial cells-mediated protective activity in Parkinson's Disease models," PLos One, vol. 9, No. 7, e101668 (Jul. 3, 2014).
Ardah, M. T. et al., "Ginsenoside Rb1 inhibits fibrillation and toxicity of alpha-synuclein and disaggregates preformed fibrils," Neurobiology of Disease, Feb. 2015, vol. 74, pp. 89-101.
International Search Report and Written Opinion in corresponding International Application No. PCT/IB2014/066041, dated Apr. 7, 2015, 13 pages.
European Search Report dated Oct. 18, 2018, for corresponding EP Application No. 14906044.4 (13 pgs.).
First Notification of Reasons for Refusal by Japan Patent Office dated Jul. 31, 2018, for corresponding JP Application No. 2017-525594 with English Translation (13 pgs.).
Second Office Action, Japanese Patent Application No. 2017-525594, dated Apr. 2, 2019, 9 pages.

* cited by examiner

*Primary Examiner* — Maureen Wallenhorst
(74) *Attorney, Agent, or Firm* — Fitch, Even, Tabin & Flannery LLP

(57) ABSTRACT

The present invention describes the use of the Chinese medicinal compounds ginsenoside RB1, dihydromyricetin and salvianohc acid B, for use in diagnosing, monitoring and treating synucleinopathies, such as Parkinson's disease, in patients.

6 Claims, 14 Drawing Sheets

GN RB1: α-syn 1:1  GN RB1: α-syn 2:1  GN RB1: α-syn 4:1

SAB: α-syn 1:1  SAB: α-syn 2:1  SAB: α-syn 4:1

DHM: α-syn 1:1  DHM: α-syn 2:1  DHM: α-syn 4:1

COMPOUNDS FOR USE AS IMAGING AGENTS

TECHNICAL FIELD

This invention relates to compounds isolated from Chinese herbal medicines and the use of these compounds for detecting the presence of α-synuclein aggregates and in diagnosing and monitoring synucleinopathic disorders. The invention also relates to the use of the compounds in the treatment of synucleinopathic disorders.

BACKGROUND

Diseases associated with abnormalities in synucleins are often referred to as the synucleinopathies. Synucleinopathies include the neurodegenerative conditions, Parkinson's disease (PD), dementia with Lewy bodies (DLB), and multiple system atrophy (MSA).

Synucleins are a family of small proteins, about 14 kDa that are expressed at high levels in nervous tissues. Three members of the family are α-, β-, and γ-synucleins. α-Synuclein is expressed mainly in brain tissues and is primarily located at the presynaptic terminal of neurons. α-Synuclein normally exists as a soluble monomeric protein but can adopt several different folded confirmations depending on its environment. Monomeric α-synuclein can also aggregate into oligomers and into higher molecular weight insoluble fibrils. α-Synuclein aggregation proceeds from monomeric α-synuclein through to the formation of soluble oligomers (early aggregates), which then converts into higher molecule weight ordered fibrils (late aggregates).

In synucleinopathies it has been shown that soluble α-synuclein oligomers in brain homogenates of PD and DLB are elevated compared to normal brains. While neuropathological studies of PD have revealed the presence of cytoplasmic inclusions found in the degenerating dopaminergic neurons of the substantia nigra and other cortical and subcortical neurons. These lesions in the brain are known as Lewy bodies and Lewy neurites and have also been shown to constitute the main pathological features in the brain of DLB patients. These neuropathologic lesions often characterise the end stage of PD and DLB have largely been found to be composed of fibrillar α-synuclein deposits. Additional studies have shown that α-synuclein is also associated with pathological lesions in other neurodegenerative diseases sometimes involving non-neuronal cells, such as the cytoplasmic inclusions found in MSA.

Chinese medicinal compositions derived from medicinal herbs and plants have been used in the treatment of a wide range of diseases for many hundreds of years. Traditional Chinese medicine has been used as remedies for various disorders including dementia and other neurodegenerative disorders. Effort has been put into determining the pharmacological basis behind traditional Chinese medicinal compositions.

Ginseng is one Chinese medicinal composition that has been studied. The pharmacological properties of ginseng are mainly attributed to its biologically active ingredients, the ginsenosides. The ginsenosides can be extracted from many parts of the ginseng plant including the root, leaves and ginseng berries. Ginsenosides are derivatives of triterpenoid dammarane with a four-ring, steroidal structure bearing sugar moieties and an aliphatic side chain.

Another Chinese medicinal composition is danshen. Pharmacological properties of danshen have been attributed to salvianolic acid B and its anti-oxidative ability. A further Chinese medicinal composition is the Japanese raisin tree. The pharmacological properties of the Japanese raisin tree have been attributed to dihydromyricetin, a flavonoid, and the compound has been used as a hangover cure.

WO2009/027690 discloses peptides that bind α-synuclein and mentions their use in the diagnosis and monitoring of synucleinopathic diseases. WO03/69332 and WO99/50300 discloses method of detecting α-synuclein oligomerisation using monoclonal antibodies.

This invention aims to provide further compounds that can be used in the imaging and/or diagnosing of synucleinopathies in subjects.

SUMMARY OF INVENTION

The invention is directed to compounds having the ability to bind and disaggregate α-synuclein fibrils.

The compounds, ginsenoside Rb1, dihydromyricetin and salvianolic acid B, found in plants used in traditional Chinese medicine have been found to bind and disaggregate α-synuclein aggregates.

Accordingly the invention is directed to an imaging agent for use in detecting α-synuclein aggregates comprising a compound selected from ginsenoside Rb1, dihydromyricetin, or salvianolic acid B, and a detectable label.

Further provided is a method of detecting α-synuclein aggregates, the method comprising:
administering a compound selected from ginsenoside Rb1, dihydromyricetin, or salvianolic acid B; and
detecting the binding of the compound to α-synuclein aggregates.

The method can be an in vitro method or an in vivo, i.e. in a subject. In one embodiment of an in vitro method the method comprises administering the compound to a sample obtained from a subject.

The invention further provides a method of imaging α-synuclein aggregates comprising detecting the binding of the compound ginsenoside Rb1, dihydromyricetin, or salvianolic acid B to α-synuclein aggregates. The method for imaging aggregates can comprise administering a compound selected from ginsenoside Rb1, dihydromyricetin, or salvianolic acid B; and detecting the binding of the compound to α-synuclein aggregates.

The method may be for imaging α-synuclein aggregates in a sample, or for imaging α-synuclein aggregates in a subject. In a method for imaging α-synuclein aggregates in vitro the method can comprise administering the compound to a sample obtained from a subject. In one embodiment the sample can be a brain tissue sample.

In a method for imaging α-synuclein aggregates in a subject, the method can comprise administering the compound to a subject. In one embodiment the method can comprise administering the compound by non-surgical means.

The compound being detected can comprise a detectable label. The presence of the binding of the compound to α-synuclein fibrils can be detected by autoradiography, positron emission tomography, magnetic resonance imaging, a gamma counter, or a scintillation counter.

The invention further provides a method of diagnosing a synucleinopathic disease comprising detecting the presence or absence of α-synuclein aggregates. The presence of α-synuclein aggregates indicates that the subject has a synucleinopathic disease and the absence of α-synuclein aggregates indicates that the subject does not have the synucleinopathic disease.

The method of diagnosing a synucleinopathic disease can comprise the steps of:

combining in vitro a sample of tissue and/or a biological fluid from the subject with a compound selected from ginsenoside Rb1, dihydromyricetin, or salvianolic acid B; and detecting the presence or absence of aggregates of α-synuclein in the sample.

The invention also provides an in vitro method of diagnosing a synucleinopathic disease involving α-synuclein and/or fragment(s) of α-synuclein, the method comprising the steps of:

(a) combining in vitro a sample of tissue and/or biological fluid from the patient with a compound selected from ginsenoside Rb1, dihydromyricetin, or salvianolic acid B under conditions effective to allow binding of the compound to aggregates of α-synuclein present in the sample; and (b) detecting the presence or absence of aggregates of α-synuclein in said sample, wherein the presence of α-synuclein aggregates indicates that the subject has a synucleinopathic disease and the absence of α-synuclein aggregates indicates that the subject does not have said synucleinopathic disease.

An alternative method of diagnosing a synucleinopathic disease in a subject comprises the steps of:

administering a compound selected from ginsenoside Rb1, dihydromyricetin or salvianolic acid B to the subject;

detecting the presence or absence of aggregates of α-synuclein in the subject.

The compound may be administered to the subject by a non-surgical method.

The invention further provides a method for disaggregating α-synuclein aggregates in a subject having a synucleinopathic disorder, the method comprising administering a compound selected from ginsenoside Rb1, dihydromyricetin or salvianolic acid B to the subject. The α-synuclein aggregates can be Lewy bodies or Lewy neuritis.

The invention also relates to a pharmaceutical composition comprising dihydromyricetin, ginsenoside Rb1 or salvianolic acid B, or a pharmaceutically acceptable salt or solvate thereof and a pharmaceutically acceptable diluents or carrier for disaggregating fibrils in Lewy bodies or Lewy neurites in a subject having a synucleinopathic disorder.

The invention further provides a method of inhibiting the α-synuclein fibrillation in a subject having a synucleinopathic disorder, the method comprising administering a compound selected from ginsenoside Rb1, dihydromyricetin, or salvianolic acid B to the subject.

BRIEF DESCRIPTION OF THE FIGURES

FIG. 3D shows the results of α-synuclein fibrils aged alone.

(FIG. 9A—Gn Rb1 (50 µM), Scale bar, 1,000 nm. FIG. 9B—salvianolic acid B (SAB) or dihydromyricetin (DHM), compound: α-synuclein at 6:1, Scale bar, 500 nm.)

FIG. 10A shows the gel filtration profile of the 5-day aggregated α-synuclein in the presence of Gn Rb1 (α-synuclein concentration=100 µM)-using a superdex 200 SE column. The elution was monitored at the absorbance wavelength of 215 nm. FIG. 10B shows the immunoblot analysis of the samples P1, P2 and P3 separated by electrophoresis in a 15% SDS-PAGE gel. FIG. 10C shows the electron microscopy images of negatively stained samples P1, P2 and P3 of α-synuclein in the presence of Gn Rb1 purified by SEC.

Scale bar represents 500 nm. FIG. 10D shows the UV absorbance spectra of P1, P2 and P3. The UV absorbance was recorded between 200-600 nm employing a 10 mm quartz cuvette.

FIG. 11A shows the gel filtration profile of 100 μM α-synuclein sample incubated with dihydromyricetin for 5 days using a superdex 200 SE column. The elution was monitored at absorbance wavelengths of $A_{215}$. FIG. 11B shows the immunoblot analysis of the samples P1, P2 and P3 separated by electrophoresis in a 15% SDS-PAGE gel. FIG. 11C shows the electron microscopy images of negatively stained samples P1, P2 and P3 of α-synuclein in the presence of dihydromyricetin purified by SEC. FIG. 11D shows the UV absorbance spectra of P1, P2 and P3 samples from the SE chromatography. The UV absorbance spectra was recorded between 200 nm to 600 nm using a 10 mm quartz cuvette.

FIG. 12A shows the gel filtration profile of 100 μM α-synuclein sample incubated with salvianolic acid B at 4:1 molar ratio for 5 days using a superdex 200 SE column. The elution was monitored at absorbance wavelengths of $A_{215}$. FIG. 12B shows the immunoblot analysis of the samples P1, P2 and P3 separated by electrophoresis in a 15% SDS-PAGE gel. FIG. 12C shows the electron microscopy images of negatively stained samples P1, P2 and P3 of α-synuclein in the presence of salvianolic acid B purified by SEC. FIG. 12D shows the UV absorbance spectra of P1, P2 and P3 samples from the SE chromatography. The UV absorbance spectra was recorded between 200 nm to 600 nm using a 10 mm quartz cuvette.

FIG. 13A—all scans, FIG. 13B—1:1, FIG. 13C—4:1, and FIG. 13D—6:1).

DETAILED DESCRIPTION OF THE INVENTION

Figure 1A:
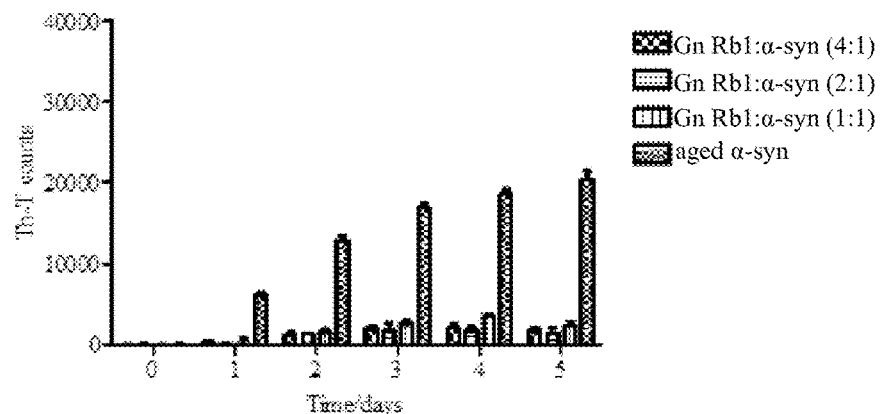
FIGS. 1A-1C show inhibition of α-synuclein fibrillation, including by ginsenoside Rb1 (Gn Rb1) (FIG. 1A), salvianolic acid B (FIG. 1B) and dihydromyricetin (FIG. 1C). Samples of α-synuclein (25 µM) were incubated for 5 days at 37° C. with continuous shaking in the presence of various concentrations of the compounds (100 µM, 50 µM and 25 µM). Fibril formation was measured by Th-T binding assay. The assay was performed in triplicate, and the means±standard deviations are shown.

The compounds ginsenoside Rb1, dihydromyricetin and salvianolic acid B, found in traditional Chinese medicinal compositions have been found to bind and disaggregate α-synuclein aggregates. Accordingly the invention is directed to the use of ginsenoside Rb1, dihydromyricetin and salvianolic acid B in methods of detecting α-synuclein aggregates. The compounds can also be used as imaging agents in detecting α-synuclein aggregates.

By α-synuclein aggregates it is meant mature insoluble aggregates of α-synuclein fibrils, including but not limited to α-synuclein deposits such as Lewy bodies and Lewy neurites. The aggregates may also comprise other components.

Due to the ability of the compounds to bind to and disaggregate performed α-synuclein fibrils the compounds are suitable for use in the imaging of α-synuclein aggregates and/or in diagnosing of diseases involving α-synuclein.

Without being bound by theory, the compounds can bind the fibrils in the aggregates and causes the pre-formed fibrils to disaggregate, which enables the fibril-compound complexes formed to be detected for imaging and diagnostic purposes.

Suitable compounds for use in detecting and imaging α-synuclein deposits and for use in diagnosing synucleinopathic diseases include ginsenosides such as ginsenoside Rb1, having the structure as shown in formula (I):

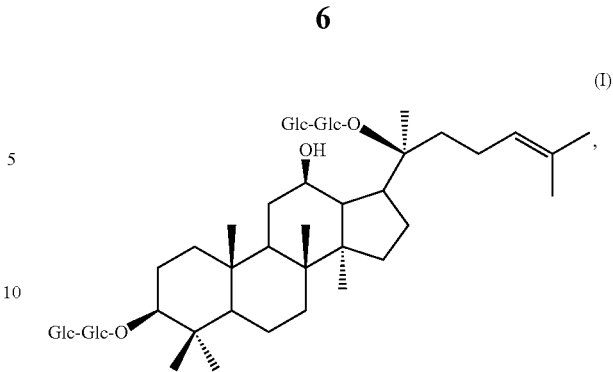

dihydromyricetin, having the structure as shown in formula (II):

(II)

and salvianolic acid B, having the structure as shown in formula (III):

(III)

The compounds can be labelled to facilitate imaging of α-synuclein aggregates. The compounds can for example include a detectable label. The detectable label is typically one which enables the detection of the compound when bound to the α-synuclein fibrils. Useful labels include fluorescent labels, radiolabels and contrast agents.

Suitable radiolabels include $^{18}F$, $^{123}I$, $^{111}In$, $^{131}I$, $^{14}C$, $^{3}H$, $^{99m}Tc$, $^{32}P$ and $^{125}I$. Suitable fluorescent labels include fluorescein and rhodamine. Suitable contrast agents include rare earth ions such as gadolinium (Gd), dysprosium and iron, and magnetic agents. Other labels include nuclear magnetic resonance active labels, positron emitting isotopes detectable by a positron emission tomography (PET) scanner, chemiluminescent and enzymatic markers. The detectable label may be attached to the compound directly or via linker. Alternatively the detectable label may be incorporated into the structure of the compound.

The compounds, ginsenoside Rb1, dihydromyricetin or salvianolic acid B, can be labelled with the above and other detectable labels using standard techniques.

The compounds, ginsenoside Rb1, dihydromyricetin and salvianolic acid B comprising a detectable label are useful in methods of imaging α-synuclein aggregates. The presence or absence of the α-synuclein aggregates may be detected in the subject in vivo, for example in the brain, using any suitable imaging techniques. The subject is typically a mammal, preferably a human. The subject may be an experimental animal in particular an experimental animal model of synucleinopathic disease. Animal models of, for example Parkinson's Disease are known in the art and include transgenic mice.

Suitable imaging techniques include PET, gamma-scintigraphy, magnetic resonance imaging (MRI), functional magnetic resonance imaging (FMRI), magnetoencephalography (MEG) and single photon emission computerized tomography (SPECT). MRI and Pet are preferred methods for in vivo imaging.

The presence or absence of the α-synuclein aggregates may also be detected in vitro, for example to identify agents that inhibit α-synuclein aggregation or in biological samples taken from the subject.

Therefore other imaging methods may include microscopy, such as electron microscopy, confocal microscopy or light microscopy.

The α-synuclein aggregates may be detected in vitro or in vivo, by administering ginsenoside Rb1, dihydromyricetin or salvianolic acid B, and detecting the binding of the compound to α-synuclein fibrils of the aggregates.

The α-synuclein aggregates to be detected may be present in the body fluids or tissues or other samples to be tested, including but not limited to aggregates present in the brain of a living mammal or in a brain sample obtained from the subject to be tested. The method can also be carried out on other body tissues or body fluids, such as heart or gastrointestinal tissue. In particular in vitro methods can be carried out on tissue or biological fluid samples.

The sample is combined with the compound, ginsenoside Rb1, dihydromyricetin or salvianolic acid B, for a time and under conditions effective to allow binding of the compound to any α-synuclein aggregate present in the sample. Preferably the sample is combined with the compound for a time and under conditions effective to allow binding of the compound to the fibrils in a Lewy body.

The sample may be processed prior to being assayed using standard methods.

The in vitro methods of detecting α-synuclein aggregates also include the use of the compounds, ginsenoside Rb1, dihydromyricetin or salvianolic acid B, in detecting α-synuclein aggregates in samples to determine the effectiveness of other compounds to disaggregate α-synuclein and/or have an effect on the formation α-synuclein aggregates.

The compounds ginsenoside Rb1, dihydromyricetin and salvianolic acid B, can be used in methods of diagnosing synucleinopathies. A method of diagnosing a synucleinopathic disease can comprise detecting the presence or absence of α-synuclein aggregates. The presence of α-synuclein aggregates indicates that the subject has a synucleinopathic disease and the absence of α-synuclein aggregates indicates that the subject does not have the synucleinopathic disease.

The presence of absence of α-synuclein aggregates can be detected by determining whether a complex between the fibrils of the aggregate and the compound are present. The presence and or absence of complexes between the fibrils and the compound can be determined by the imaging techniques described above.

The diagnostic methods can be in vitro methods, using a tissue sample or a biological fluid from a subject. The sample is then contacted with the compound and the presence of absence of a complex between the fibrils of the aggregates and the compound is determined.

Alternatively the diagnostic methods can be in vivo methods, wherein the compound, ginsenoside Rb1, dihydromyricetin or salvianolic acid B is administered to the subject; and the presence or absence of aggregates of α-synuclein is detected in the subject. The compound may be administered to the subject by a non-surgical means.

The subject may be undergoing therapy to treat a synucleinopathic disease and the method is for monitoring the effectiveness of the treatment.

Levels of α-synuclein aggregates detected by the imaging methods may be compared with a standard to determine the status of the disease and/or whether a particular treatment has been successful. The number and/or size of α-synuclein aggregates present in the brain of the subject correlates with synucleinopathic disease progression. A decrease in the number and/or size of α-synuclein aggregates suggests the disease is regressing. An increase in the number and/or size of α-synuclein aggregates indicates the disease is progressing.

The compounds used in the method of diagnosis can be labelled as discussed above. Imaging techniques as discussed above can be used in detecting the binding of the compounds to the fibrils, in the diagnostic methods.

The formulation of the compounds for use in the imaging and diagnostic methods may depend on the method it will be used in.

The compound may be administered to the subject by non-surgical means. Non-surgical means of administration include for examples, administration orally (e.g. as tablets, troches, lozenges, aqueous or oily suspensions, dispersible powders or granules), topically, transdermally or by infusion or inhalation techniques. The doctor will be able to determine the required route of administration for each particular subject.

The compound may be administered directly to the site of an α-synuclein aggregate e.g. a Lewy body, typically by injection into a blood vessel supplying the brain or into the brain itself.

Typically the compound will be formulated with a pharmaceutical acceptable carrier or diluent. A physician will be able to determine a suitable pharmaceutical form for delivery to the subject.

A further embodiment of the invention comprises a method for disaggregating fibrils in Lewy bodies or Lewy neurites in a subject having a synucleinopathic disorder, the method comprising administering a compound selected from ginsenoside Rb1, dihydromyricetin, or salvianolic acid B to the subject. The compound may be administered in a therapeutically effective amount.

The invention also relates to a pharmaceutical composition for disaggregating fibrils in Lewy bodies or Lewy neurites in a subject having a synucleinopathic disorder, the composition comprising a dihydromyricetin, ginsenoside Rb1 or salvianolic acid B, or a pharmaceutically acceptable salt or solvate thereof, and a pharmaceutically acceptable diluent or carrier.

Without being bound by theory the ability of the compounds ginsenoside Rb1, dihydromyricetin and salvianolic acid B to bind and disaggregate fibril aggregates and to inhibit α-synuclein fibrillation and enables the compounds to be used to disaggregate Lewy bodies in a subject having a synucleinopathy.

The compound ginsenoside Rb1 has also been found to inhibit α-synuclein fibrillation. Without being bound by theory ginsenoside Rb1 is thought to bind and stabilize the structure of soluble oligomeric α-synuclein with no β-sheet content, and block α-synuclein induced toxicity. Whilst the compounds dihydromyricetin and salvianolic acid B have been found to inhibit α-synuclein oligomerization and fibrillation. Therefore these compounds are suitable in the treatment of synucleinopathic diseases.

Accordingly the invention further provides a method of inhibiting the α-synuclein fibrillation in a subject having a synucleinopathic disorder, the method comprising administering a compound selected from ginsenoside Rb1, dihydromyricetin, or salvianolic acid B to the subject. The compound may be administered in a therapeutically effective amount.

A synucleinopathic disease or disorder or synucleinopathy is a disease involving synucleins, in particular α-synuclein. Synucleinopathies include but are not limited to diseases selected from the group comprising Parkinson's disease, dementia with Lewy bodies, and multiple system atrophy. Preferably the subject has Parkinson's disease or dementia with Lewy bodies.

A "therapeutically effective amount" of a compound is an amount of the compound, which when administered to a subject, is sufficient to confer the intended therapeutic effect. A therapeutically effective amount can be given in one or more administrations.

Pharmaceutical forms suitable for the delivery of the compounds of the present invention and methods of preparing the various pharmaceutical compositions will be readily apparent to those skilled in the art. Such compositions and methods for their preparations may be found, for example in Remington's Pharmaceutical Sciences, 19th Edition (Mack Publishing Company 1995).

Suitable composition forms can include forms suitable for oral administration such as tablets, capsule, pills, powders, sustained release formulations, solutions, and suspension, for parental injection such as sterile saline solutions, suspensions or emulsion; or rectal administration such as suppositories. Exemplary parenteral administration forms include suspensions or solutions in sterile aqueous solutions, for example aqueous propylene glycol or dextrose solutions. Such dosage forms can be suitably buffered, if desired.

Suitable pharmaceutical carriers include inert diluents or fillers, water and various organic solvents. Compositions may also include additional ingredients such as flavouring, binders, and excipients. Tablets may include: disintegrates such as starch, alginic acid and complex silicates; binding agents such as sucrose, gelatine and acacia, and lubricating agents such as magnesium stearate, sodium lauryl sulphate and talc.

Solid compositions may also include soft and hard gelatin capsules. Preferred materials include lactose, milk sugars and high molecular weight polyethylene glycols.

Aqueous suspensions or elixirs may include sweetening or flavouring agents, colours and dyes, emulsifying agents, suspending agents as wells as diluents such as water, ethanol, propylene glycol, glycerin or combinations thereof.

The following Examples illustrate the invention.

Example 1

Expression and Purification of Recombinant Human α-Synuclein.

A GST-α-synuclein fusion construct in the pGEX-4T1 vector (provided by Dr. Hyangshuk Rhim of The Catholic University College of Medicine, Seoul, Korea) was inserted into BL21 *E. coli* bacteria by heat shock. The transformed bacteria were grown in LB medium supplemented with 0.1 mg/ml ampicillin at 37° C. in an orbital shaker to an $OD_{600}$ of 0.5. Expression was then induced by adding 0.5 mM IPTG (Sigma-Aldrich Chemie GmbH, Germany), and the culture was incubated for 2 hours at 37° C. The cells were harvested by a 15 minute centrifugation at 9000×g, and the resulting pellet was then resuspended in lysis buffer (50 mM Tris-HCl, pH 7.4, 150 mM NaCl, 2 mM EDTA, 1% NP-40, 0.1% DTT) and shaken for 10 minutes at room temperature. To improve the efficiency of cell lysis, the resuspended pellet was subjected to 6 freeze-thaw cycles in liquid nitrogen and a 37° C. water bath. The lysate was then centrifuged at 27,000×g for 15 minutes, and the resulting supernatant was retained for purification by affinity chromatography using sepharose beads conjugated to glutathione, which has a high affinity for the GST tag. The cell lysate was mixed with glutathione sepharose beads and incubated for 1 hour at room temperature, followed by centrifugation at 500×g at 4° C. for 8 minutes. The beads were then washed twice with wash buffer (50 mM Tris-HCl, 150 mM NaCl, 10 mM EDTA, 1% Triton X-100, pH 8.0); twice with 50 mM Tris-HCl, pH 8.0; and once with 1×PBS. The washed beads were resuspended in 5 ml of 1×PBS, and the GST tag was cleaved by human plasma thrombin (1 unit/µL), (Sigma-Aldrich, USA). The thrombin-catalyzed cleavage reaction was incubated overnight at room temperature with continuous mixing followed by a 5 minute incubation at 37° C. The reaction mixture was then centrifuged for 8 minutes at 500×g at 4° C., and benzamidine sepharose beads (Amersham, Sweden) were used to 'fish out' thrombin. Pure α-synuclein was collected by centrifugation at 500×g for 8 minutes at 4° C. The α-synuclein concentration was estimated using a BCA assay (Pierce Biotechnology, Rockford, Ill.).

Aggregation of α-Synuclein In Vitro

The protein purity was estimated to be >95% using an SDS gel. Ginsenoside, Rb1, stock solutions (10 mM) were prepared in 100% DMSO, and the final amount of DMSO in the sample solutions was 1%. Samples of 25 µM α-synuclein in PBS were aged alone or with Rb1 at various molar ratios (Rb1:α-synuclein molar ratios of 4:1, 2:1 and 1:1). The samples were placed in 1.5 ml sterile polypropylene tubes, drops of mineral oil were added to prevent sample evaporation, and the tubes were then sealed with parafilm and incubated at 37° C. for 5 days with continuous shaking at 800 rpm in a Thermomixer (Eppendorf). Samples were collected at the indicated time points, and a Thioflavin-T assay was performed immediately at each time point, while the rest of the samples were stored at −80° C. until needed for further analyses.

Thioflavin-T (Th-T) Assay

α-Synuclein fibril formation was monitored by Th-T binding assay. Th-T is a fluorescent dye that interacts with fibrils containing a β-sheet structure. A total of 10 µL of each sample was diluted in 40 µL of Th-T in PBS. Fluorescence was then measured in a 384-well, untreated black micro-well plate (Nunc, Denmark) using a microplate reader (Victor X3 2030, Perkin Elmer) with the excitation and emission wavelengths set at 450 and 486 nm, respectively. To allow for background fluorescence, the fluorescence intensity of a blank PBS solution was subtracted from all readings.

Transmission Electron Microscopy (TEM)

Electron images were produced from α-synuclein aged alone or in the presence of the compounds. The samples (5 µL) were deposited on Formvar-coated 400-mesh copper grids (Agar Scientific, UK), fixed briefly with 0.5% glutaraldehyde (5 μL), negatively stained with 2% uranyl acetate (Sigma-Aldrich, USA) and examined with a Philips CM-10 TEM electron microscope.

Immunoblotting

Samples of α-synuclein (20 ng) incubated alone or with the compounds were mixed with 1× sample buffer (250 mM Tris-HCl, pH 6.8, 30% glycerol, 0.02% bromophenol blue) and then separated in 15% 1 mm SDS-PAGE gels. The separated proteins were transferred to 0.45 μm nitrocellulose membranes (Whatman Gmbh-Germany) at 90 V for 80 min. The membranes were boiled for 5 min in PBS and then blocked for 1 hour with 5% non-fat milk prepared in PBS-Tween-20 (0.05%; PBST). The membranes were incubated overnight at 4° C. with the primary mouse monoclonal anti-α-syn (211) antibody, which recognizes human α-synuclein (121-125) (Santa Cruz Biotechnology, USA), at a dilution of 1:1000. The membranes were then washed several times with PBST, followed by incubation with an HRP-conjugated goat anti-mouse antibody (Dako Ltd., Ely, UK) at a dilution of 1:70,000 for 60 minutes at room temperature with gentle agitation. The membranes were then extensively washed for 25 min, and immunoreactive bands were visualized with the Super Signal West Femto Chemiluminescent Substrate Kit (Pierce, Rockford, USA) according to the manufacturer's instructions.

Congo Red Binding Assay

CR is a dye with high affinity for amyloid fibrils. Congo red (20 μM) was prepared in PBS (pH 7.4) and filtered through a 0.45 μm filter. Samples of α-synuclein (5 μM), aged alone or with the compounds at different molar ratios, were mixed with Congo red (final concentration 5 μM), and the reaction samples were thoroughly mixed. The UV absorbance spectrum was recorded between 400 and 600 nm in a spectrophotometer (DU-800, Beckman-Coulter) using 10-mm quartz cuvettes (HellmaAnalytics-Germany). Congo red alone was used as blank.

Tissue Culture of BE(2)-M17 Human Neuroblastoma Cells

BE(2)-M17 human neuroblastoma cells were routinely cultured in Dulbecco's MEM/Nutrient Mix F-12 (1:1) (Gibco BRL, Rockville, Md.) containing 15% fetal bovine serum and 1% penicillin-streptomycin (P/S; 100 U/ml penicillin, 100 mg/ml streptomycin). The cells were maintained at 37° C. in a humidified incubator with 5% $CO_2$/95% air.

Measurement of Cell Viability

BE(2)-M17 cells suspended in DMEM medium were plated at a density of 15,000 cells (100 μL/well) in a 96-well plate. After 24 hours, the medium was replaced with 200 μL of OPTI-MEM (Gibco-USA) serum-free medium containing aged α-synuclein solutions with or without the compounds. Aged α-synuclein and compound-containing solutions were diluted in OPTI-MEM to obtain the desired concentration. Cells were then incubated at 37° C. in 5% $CO_2$ for 48 hours. A total of 20 μL of MTT (3-(4,5-dimethylthiazol-2-yl)-2,5-diphenyltetrazolium bromide) (Sigma-Aldrich, USA) (6 mg/ml) in PBS was dispensed into each well, and the plate was incubated at 37° C. for 4.5 hours. The MTT-containing medium was carefully removed, and 100 μL of lysis buffer (15% SDS, 50% N,N-dimethylformamide, pH 4.7) was added to each well. The lysis buffer was incubated overnight at 37° C. before the absorbance values at 590 nm were determined by a microplate reader (Perkin Elmer).

α-Synuclein Disaggregation Assay

α-Synuclein solution in PBS (pH 7.4) was aggregated at a concentration of 25 μM as indicated above. The resulting aggregated α-synuclein was incubated either alone or with Gn Rb1 or dihydromyricetin at various molar ratios (compound: α-synuclein molar ratios of 6:1, 4:1 and 2:1). It should be noted that for the purpose of the experiment, the concentration of α-synuclein taken into account was the concentration of fresh α-synuclein. The samples were incubated at 37° C. for 48 hours on a thermomixer with continuous shaking at 800 rpm. Samples were collected at regular time points, and Th-T fluorescence was measured immediately.

Seeding Polymerization Assay

The aggregation of monomeric α-synuclein with or without seeding was performed as described elsewhere. The seeds were prepared by fragmenting the mature α-synuclein fibrils by sonication to obtain short fibrils, which were employed as 'seeds'. Briefly, monomeric α-synuclein at a concentration of 100 μM was seeded with 2 μM of seeds and incubated in the presence or absence of the compounds (10 μM or 50 μM) at 37° C. for 6 hours with continuous shaking. The fibrillization was monitored by Th-T binding assay as described above.

Size Exclusion Chromatography (SEC) for Separating α-Synuclein Oligomers and Monomers SEC was carried out using an AKTA FPLC system (GE Healthcare-Sweden) and a superdex 200 column at 4° C., in order to separate the oligomers generated from the aggregation of α-synuclein with the compounds (compound: α-synuclein molar ratio of 4:1). Monomeric α-synuclein at a concentration of 100 μM was aggregated in the presence of the compounds for 5 days as described above. At the end of the aggregation process, the sample was centrifuged for 45 min at 14,000×g at 4° C. generating a supernatant free from insoluble material. Prior to injecting 80% of the generated supernatant, the column was thoroughly equilibrated with SEC running buffer (1×PBS, pH 7.4) and the flow rate was set to 0.1 ml/min (0.5 ml/fraction). The elution of α-synuclein was monitored at absorbance wavelengths of 215 nm, 254 nm, and 280 nm. To determine the elution time of monomeric α-syn, molecular weight standards (ferritin 440 kDa, aldolase 171 kDa, abmumin 68 kDa and chymotrypsinogenA 25 kDa) and monomeric α-synuclein were co-injected into the column and eluted at the same conditions mentioned above.

For the experiments with salvianolic acid B and dihydromyricetin the fractions eluting between 7-8 ml CV were combined and labeled as oligomers (sample P1), and fractions eluting between 12-14 ml CV were combined and labeled as oligomers (sample P2), whereas the fractions eluting in the 14-16 ml CV were combined and labeled as monomers (sample P3).

Whilst for the experiments with ginsenoside Rb1, the fractions eluting between 2-4 ml CV were combined and labeled as oligomers (sample P1), and fractions eluting between 10-14 ml CV were combined and labeled as oligomers (sample P2), whereas the fractions eluting in the 14-16 ml CV were combined and labeled as monomers (sample P3).

The P1, P2 and P3 fractions were further characterized by western blotting and TEM.

UV Scanning

The P1, P2 and P3 samples, representing the oligomeric and monomeric fractions of SEC, were concentrated using a speed vac (CentriVap, Labconco). Their protein content concentration was estimated by the BCA assay. The UV absorbance spectrum was recorded from 200-600 nm in a spectrophotometer (DU-800, Beckman-Coulter) using 10 mm quartz cuvettes (Hellma Analytics-Germany) and employing equal concentrations of the P1, P2 and P3. Fresh monomeric α-synuclein was used as negative control.

NMR Studies

For NMR studies, recombinant $^{15}$N-labeled α-synuclein was expressed and purified as previously described, resuspended in PBS buffer at pH 6.6. Two-dimensional $^1$H-$^{15}$N HQSC spectra were acquired for α-synuclein at 100 μM concentration in the absence of Gn Rb1 and in the presence of increasing Gn Rb1: α-synuclein stoichiometries of 1:1, 4:1 and 6:1. Data were collected on a Bruker 900 MHz spectrometer equipped with a cold probe.

Example 2

The Effect of Ginsenoside Rb1, Salvianolic Acid B and Dihydromyricetin on α-Synuclein Fibrillation α-Synuclein solution at a concentration of 25 μM was incubated at 37° C. with continuous shaking for 5 days, leading to fibril formation, which was monitored by Th-T fluorescence at regular time intervals. α-Synuclein was incubated with each of Gn Rb1, salvianolic acid B and dihydromyricetin at molar ratios of 4:1, 2:1 and 1:1 (molar ratio Compound: α-synuclein) with a constant α-synuclein concentration of 25 μM.

Gn Rb1 exhibited a significant inhibitory effect on α-synuclein fibrillation as indicated by the reduced Th-T fluorescence at all tested concentrations (FIG. 1A). This effect was observed as early as 2 days of incubation, when the inhibition percentage was approximately 90%. After 5 days of incubation, the fibrillation of α-synuclein was reduced by approximately 80%.

Figure 2A:
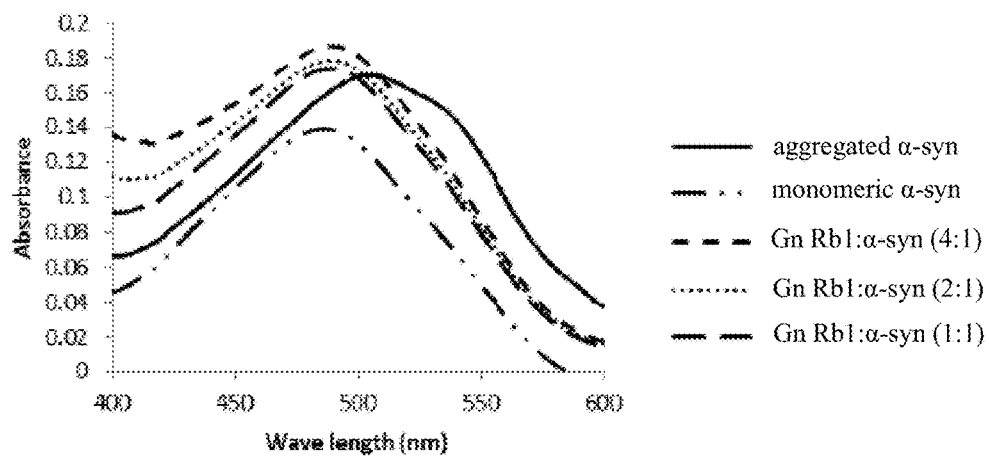
FIGS. 2A-2C show the results of the Congo red binding assay, including for Gn Rb1 (FIG. 2A), salvianolic acid B (FIG. 2B) and dihydromyricetin (FIG. 2C). α-Syn (5 µM) aged alone or in the presence of different concentrations of ginsenosides was mixed with Congo red (final concentration of 5 µM). The UV absorbance spectrum was recorded from 400 to 600 nm in a spectrophotometer.

The ability of Gn Rb1 to block α-synuclein fibril formation was further assessed by the Congo red (CR) binding assay, as described above. Upon binding to α-synuclein fibrils, the absorption maximum of CR shifts from 490 to 508 nm. This shift was quite pronounced for the α-synuclein control sample incubated in the absence of any Gn Rb1 (FIG. 2A). However, this characteristic shift was not observed for α-synuclein samples aged in the presence of Gn Rb1, indicating that this compound inhibited the formation of amyloid fibrils (FIG. 2A). Indeed, the absorption maximum of CR bound to the α-synuclein samples containing Gn Rb1 (at all tested concentrations) only shifted a few nm and did not exceed the wavelength of 495 nm (FIG. 2A). Interestingly, the CR shift was comparable to the shift observed for monomeric α-synuclein.

Figure 3A:
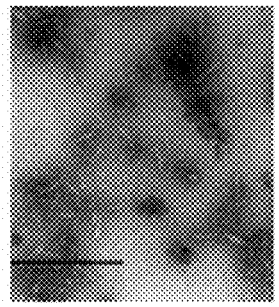
FIGS. 3A-3D show the electron microscopy images of negatively stained samples of α-synuclein (25 µM) aged alone or in the presence of Gn Rb1 (FIG. 3A), salvianolic acid B (SAB) (FIG. 3B) and dihydromyricetin (DHM) (FIG. 3C), at compound α-syn molar ratios of 4:1, 2:1, and 1:1, for 5 days with continuous shaking at 37° C. Scale bar, 500 nm.
Figure 3A:
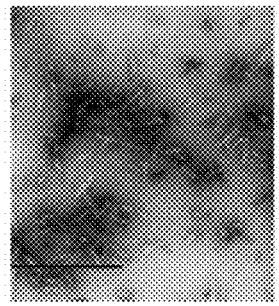
Figure 3A:
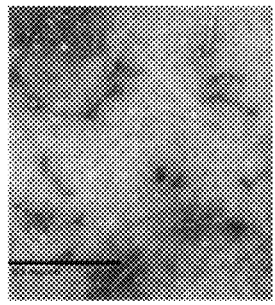

These findings were further confirmed by electron microscopy. TEM images of α-synuclein aged in the presence of Gn Rb1 showed that α-synuclein formed thin, short rod-like fibrils, with a fragmented appearance (FIG. 3A), unlike the dense meshes of long fibrils formed by α-synuclein aged alone.

Figure 1B:
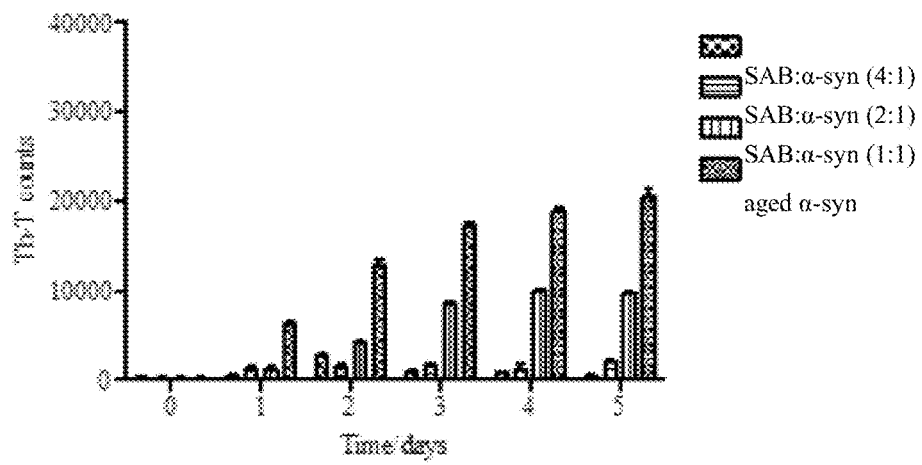

Salvianolic acid B and dihydromyricetin, inhibited α-synuclein fibrillation as indicated by reduced Th-T fluorescence (FIGS. 1B and C). At concentrations of 100 and 50 μM, salvianolic acid B exhibited a complete inhibitory effect, which was prominent beginning on the third day of incubation. After 5 days of incubation, salvianolic acid B at 100 μM completely abolished the fibrillation of α-synuclein, while at 50 μM, it inhibited fibrillation by almost 80%. At a lower concentration (i.e., 25 μM), salvianolic acid B also induced the inhibition of α-synuclein fibrillation, the percentage of which was reduced by approximately 35% after 5 days of incubation (FIG. 1B). These results indicate that salvianolic acid B inhibited the formation of fibrils in a concentration-dependent manner.

Figure 1C:
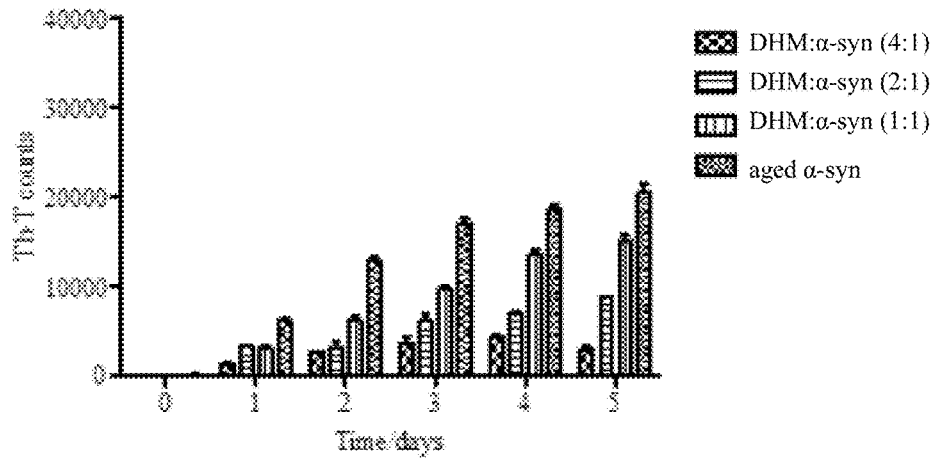

Dihydromyricetin was observed as a good inhibitor of fibrillation. After 5 days of incubation, dihydromyricetin inhibited α-synuclein fibrillation by 80 and 40% at 100 and 50 μM, respectively, while at 25 μM, the compound failed to inhibit fibrillation (FIG. 1C).

Figure 2B:
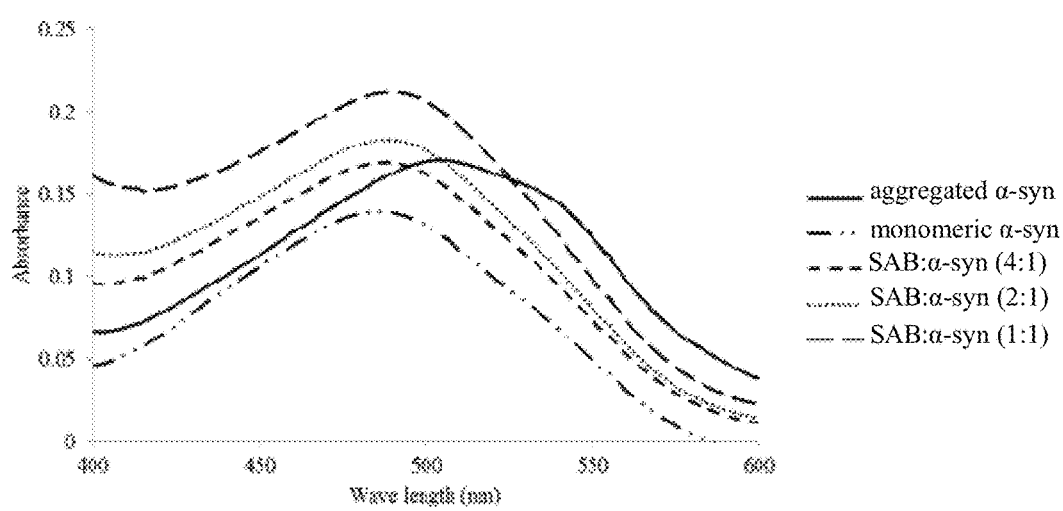
Figure 2C:
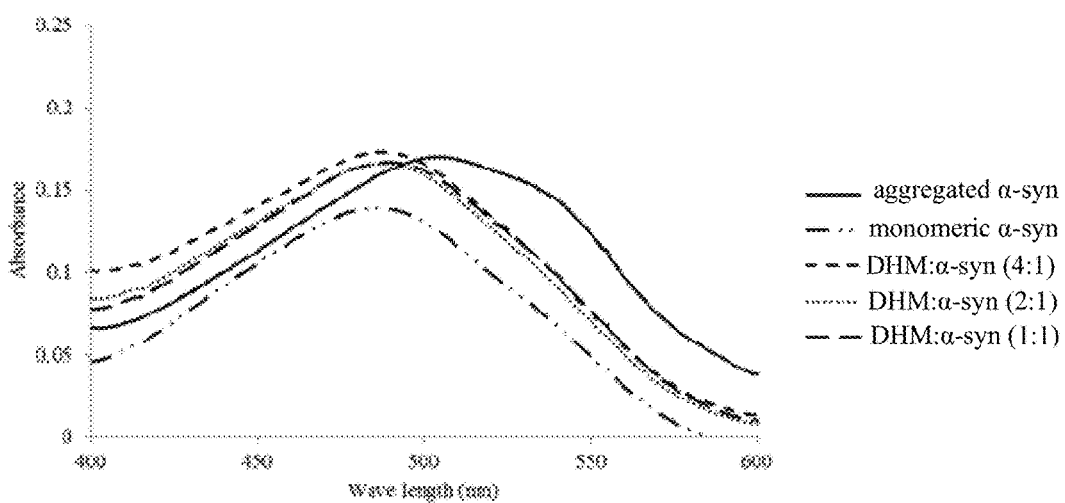

The ability of salvianolic acid B and dihydromyricetin to block α-synuclein fibril formation was further explored using the Congo red (CR) binding assay. Upon binding to α-synuclein fibrils, the absorption maximum of CR shifts from 490 to 508 nm, and this shift is quite pronounced for α-synuclein samples incubated in the absence of the compounds (FIGS. 2B and C). However, this characteristic shift was not observed for α-synuclein samples aged in the presence of salvianolic acid B or dihydromyricetin, indicating that these compounds inhibited the formation of amyloid fibrils (FIGS. 2B and C). The absorption maximum of CR bound to the α-synuclein samples containing salvianolic acid B and dihydromyricetin (at all tested concentrations) only shifted a few nm and did not exceed the wavelength of 495 nm (FIGS. 2B and C).

Figure 3B:
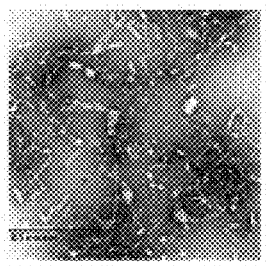
Figure 3B:
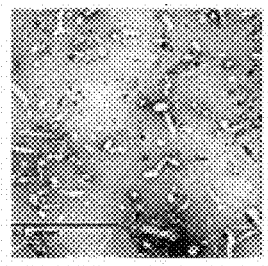
Figure 3B:
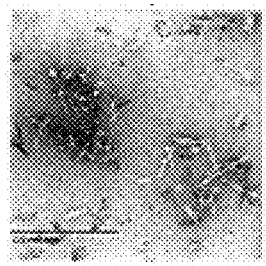
Figure 3C:
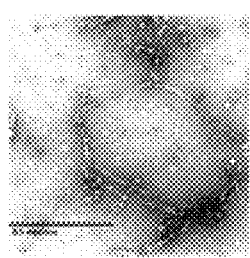
Figure 3C:
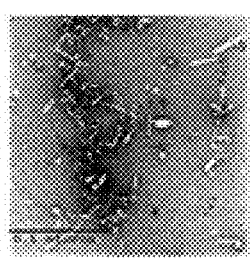
Figure 3C:
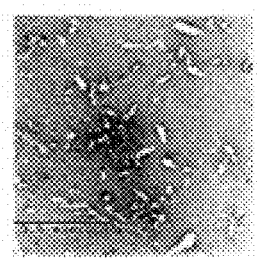
Figure 3D:
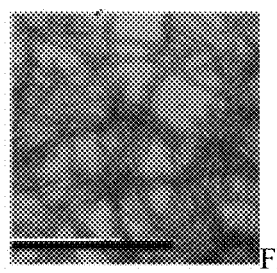

These findings were further confirmed by electron microscopy. TEM images of α-synuclein aged in the presence of salvianolic acid B and dihydromyricetin showed that α-synuclein formed thin, short rod-like fibrils, with a fragmented appearance (FIGS. 3B and C), which was unlike the dense meshes of long fibrils formed by α-synuclein aged alone (FIG. 3D).

Example 3

The Effect of Ginsenosides Rb1 Salvianolic Acid B and Dihydromyricetin on α-Synuclein on Oligomerization The effect of Gn Rb1, salvianolic acid B and dihydromyricetin on α-synuclein oligomerization was assessed by immunoblot analysis. Fresh and aged solutions of α-synuclein alone or in the presence of Gn Rb1, salvianolic acid B or dihydromyricetin were analyzed. Samples were separated in 15% SDS gels, transferred onto a nitrocellulose membrane and probed with an antibody that recognizes the amino acid residues 121-125 of α-synuclein. The majority of freshly prepared α-synuclein migrated as a band at ~16 KDa, corresponding to α-synuclein monomers (FIGS. 4A-C).

The amount of monomeric α-synuclein in the α-synuclein aged alone samples and in the presence of compounds was quantified against a fresh α-synuclein sample that contained only the monomeric species using ImageJ software.

Figure 4A:
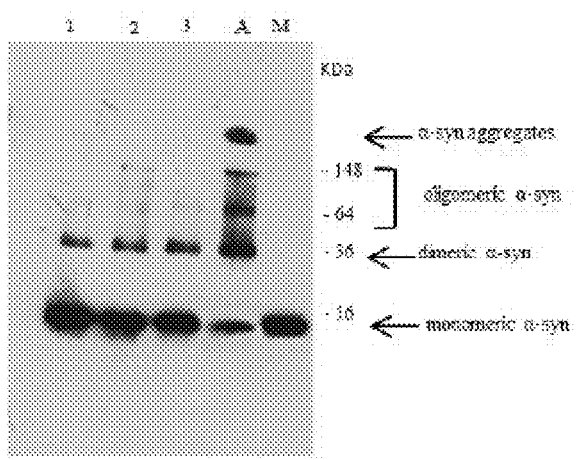
FIGS. 4A-4C show the immunoblot analysis showing the effect of Gn Rb1 (FIG. 4A), salvianolic acid B (FIG. 4B) and dihydromyricetin (FIG. 4C), on α-synuclein oligomerization. α-Syn alone or in the presence of the compounds at compound: α-syn molar ratios of 1:1, 2:1 and 4:1, was incubated for 5 days. Lane 1, compound: α-syn 1:1, lane 2, compound: α-syn 2:1, lane 3, compound: α-syn 4:1, A: aged α-syn and M: fresh α-syn.
Figure 4B:
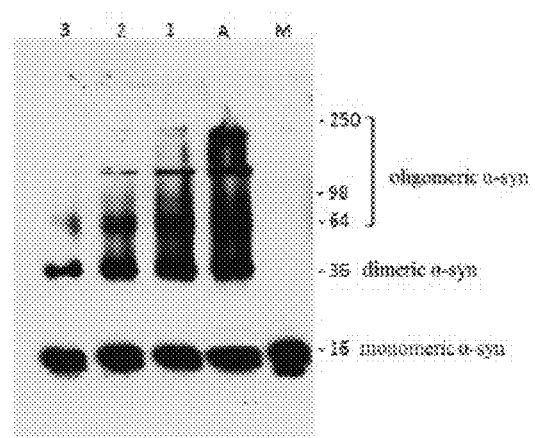
Figure 4C:
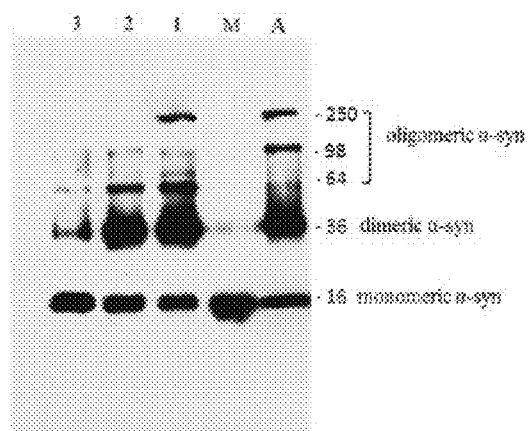
Figure 5A:
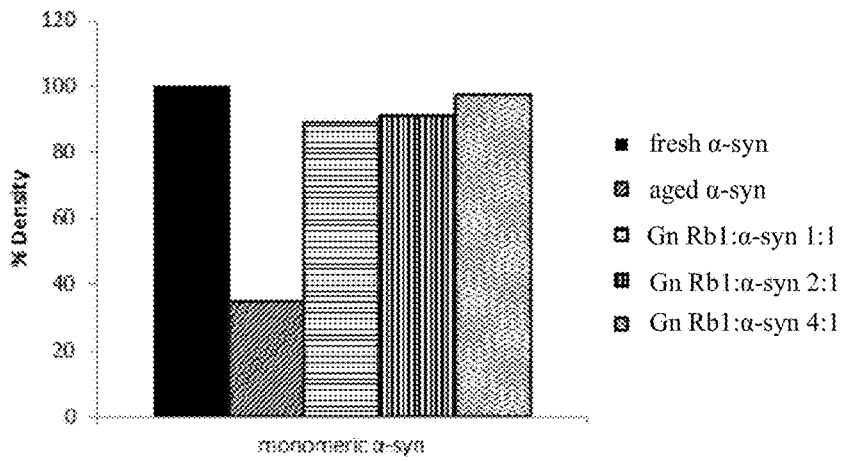
FIGS. 5A-5C show the amount of the monomeric α-synuclein in the samples of FIGS. 3A-3C quantified using ImageJ software.
Figure 5B:
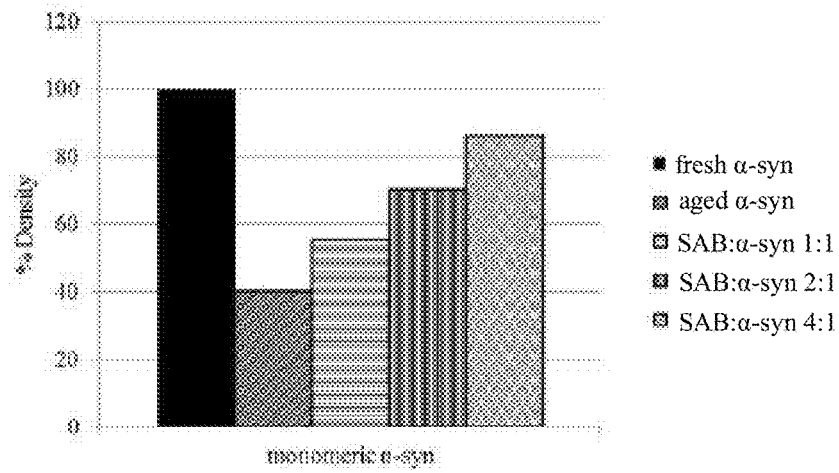
Figure 5C:
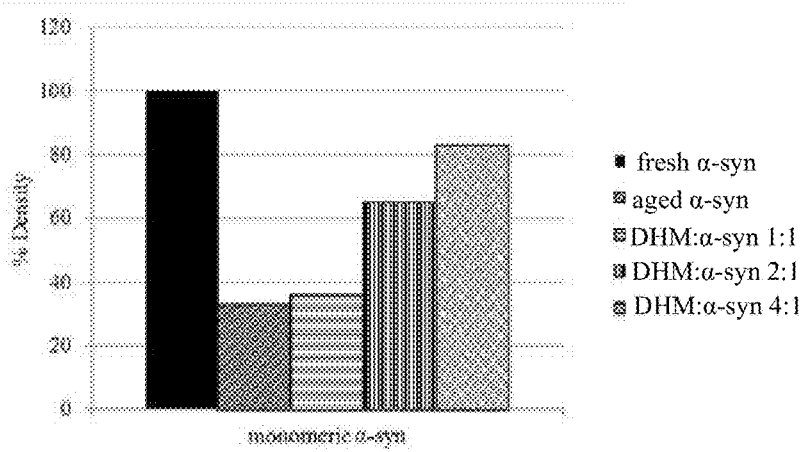

Gn Rb1, was shown to be a potent inhibitor of α-synuclein oligomerization at all molar ratios (FIGS. 4A and 5A) Gn Rb1 inhibited the formation of larger aggregates (MW>250 kDa) and high MW oligomers, generating a prominent monomeric band and a weak dimeric band (FIG. 4A). Densitometric analysis of the monomeric bands revealed that Gn Rb1 hindered α-synuclein oligomerization to the same extent in all tested concentrations, (FIG. 5A). Even at the lowest concentration, Gn Rb1 was able to inhibit the formation of larger aggregates.

Salvianolic acid B and dihydromyricetin, were shown to be potent inhibitors of α-synuclein oligomerization. Salvianolic acid B and dihydromyricetin inhibited α-synuclein oligomerization in a dose-dependent fashion (FIGS. 4B-C and 5B-C).

Salvianolic acid B inhibited the formation of larger aggregates (MW>250 kDa) and high MW oligomers; bands corresponding to monomeric and dimeric α-synuclein were the most prominent species, and a band corresponding to trimeric α-synuclein was faint (FIG. 4A). With decreasing salvianolic acid B concentration, the dimeric, trimeric and oligomeric bands were increasingly stronger, indicating that salvianolic acid B inhibited α-synuclein oligomerization in a dose-dependent fashion (FIG. 4A). Even at the lowest concentration, salvianolic acid B still induced the inhibition of larger aggregates. Dihydromyricetin also suppressed the formation of oligomeric forms in a concentration-dependent manner; the highest concentration was the most potent of the three concentrations tested (FIG. 4B). At the highest concentration of dihydromyricetin, α-synuclein produced faint dimeric and trimeric bands (FIG. 4B). However, these bands were progressively stronger with decreasing CMC10 concentration, consistent with dose-dependent inhibition (FIG. 4B). These results show salvianolic acid B and dihydromyreicetin block α-synuclein oligomerization and fibrillation.

Example 4

The Effect of Ginsenosides Rb1, Salvianolic Acid B and Dihydromyricetin on α-Synuclein-Induced Cytotoxicity BE(2)-M17 human neuroblastoma cells were treated with aged α-synuclein solutions at three different concentrations, 0.5 µM, 1 µM and 5 µM, either alone or in the presence of Gn Rb1, salvianolic acid B or dihydromyricetin.

The viability of cells treated with α-synuclein aged in the presence or absence of the Gn Rb1, salvianolic acid B or dihydromyricetin was determined by the MTT assay. Prior to the experiments, the effect of the Gn Rb1, salvianolic acid B and dihydromyricetin alone on cell viability was assessed (data not shown), employing the same non-toxic Gn Rb1, salvianolic acid B and dihydromyricetin concentrations that were later employed for the experiments with aged α-synuclein.

Figure 6A:
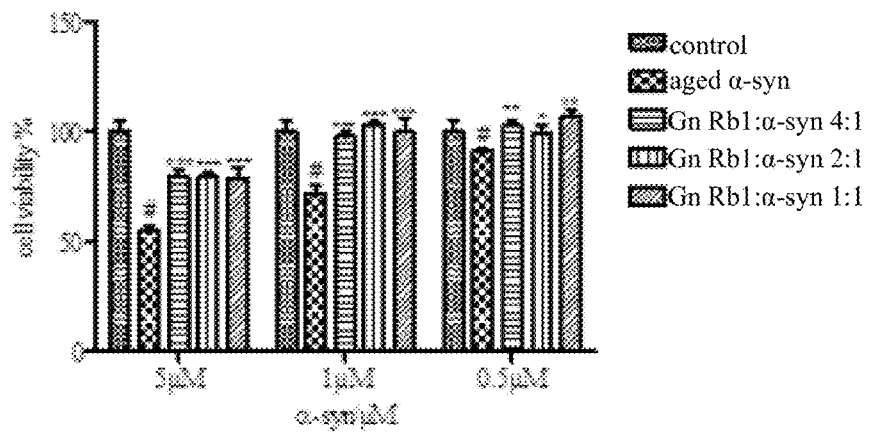
FIGS. 6A-6C show the effect of the compounds Gn Rb1 (FIG. 6A), salvianolic acid B (FIG. 6B) and dihydromyricetin (FIG. 6C) on the toxicity induced by the aggregates of α-syn. The viability of M17 human cells was estimated by MTT assay. The results are expressed as percentages of the average of the control (i.e., untreated cells). The cells were treated with either α-synuclein aged with or without the compounds for 48 hours prior to the addition of MTT (average of 3 wells±standard deviation). Statistical analysis was performed using a two-tailed unpaired t-test. *, $p<0.001$; , $p<0.01$; *, $p<0.05$.
Figure 6B:
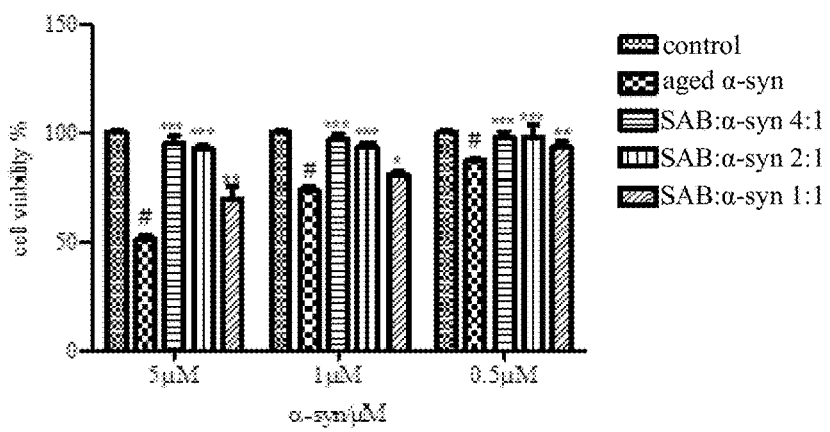
Figure 6C:
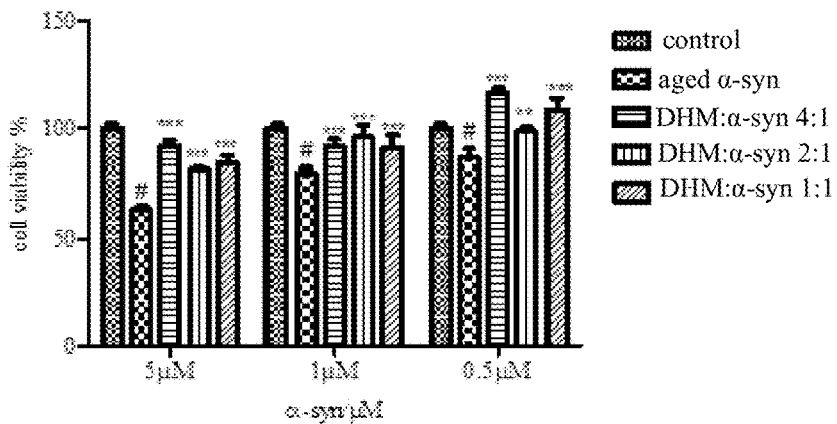

Aged α-synuclein inhibited the reduction of MTT in a dose-dependent fashion (FIGS. 6A-6C). Given that MTT reduction is directly proportional to the number of surviving cells, it becomes apparent that fewer cells survived at higher concentrations of aged α-synuclein (FIGS. 6A-6C). However, the α-synuclein aged in the presence of Gn Rb1, salvianolic acid B or dihydromyricetin was less toxic to the cells, as indicated by the increase in MTT reduction (FIGS. 6A-6C).

At 5 µM, the aged α-synuclein induced the decrease in the number of viable cells by almost 50%, whereas in the presence of all concentrations of Gn Rb1, the viability of the cells increased by approximately 30%, with approximately 80% of the cells surviving (FIG. 6A). A similar trend was observed in the case of 1 µM aged α-synuclein; in all used concentrations, Gn Rb1 improved the viability of the cells treated with 1 µM aged α-synuclein by approximately 30% (FIG. 6A).

In the presence of salvianolic acid B, approximately 95% of the cells survived for the molar ratios of 4:1 and 2:1 (FIG. 6B). At these molar ratios, salvianolic acid B had also proved to be a good inhibitor for fibril formation, as also indicated by the reduction in the Th-T counts (FIG. 1B). Dihydromyricetin also reduced the α-synuclein toxicity (FIG. 6C). Dihydromyricetin exhibited protection for cells at the highest concentration, which is represented by the molar ratio of 4:1, thus improving cell viability by approximately 10%. These findings are in accordance with the Th-T fluorescence measurements (FIG. 1C) and immunoblotting analyses (FIGS. 4A-4C).

Example 5

The Effect of Gn Rb1 and Dihydromyricetin on Preformed α-Synuclein Amyloid Fibrils Due to their high efficiency to inhibit α-synuclein fibrillation, Gn Rb1 and dihydromyricetin were assessed for their effectiveness on reversing fibrillation. 25 µM of preformed α-synuclein fibrils were incubated at 37° C. in the presence of Gn Rb1 or dihydromyricetin at varying molar ratios (compound: α-synuclein of 6:1, 4:1 and 2:1) for a period of 48 hours. By measuring the Th-T fluorescence counts (FIGS. 7A-7B), the fibril content was estimated at different time points.

Figure 7A:
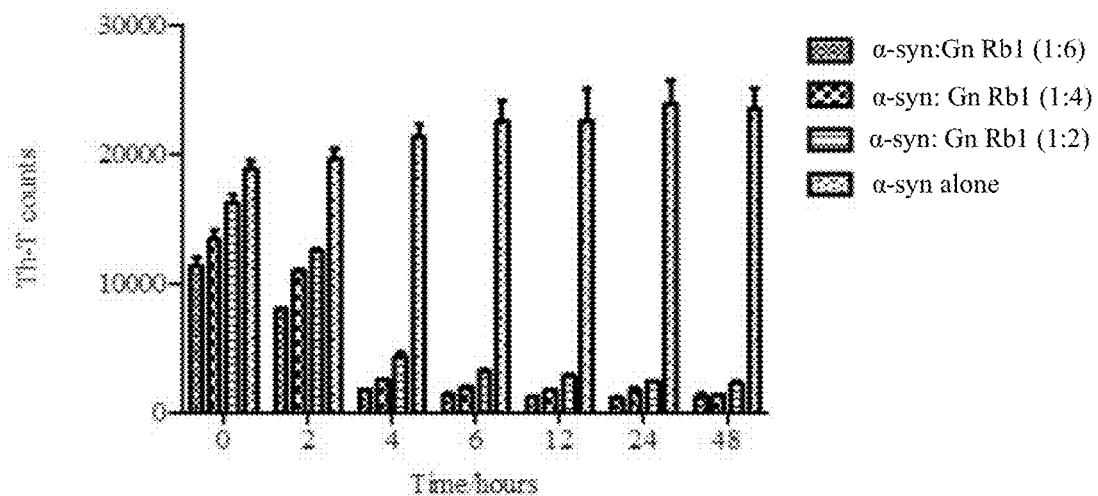
FIGS. 7A and 7B show the effect of Gn Rb1 (FIG. 7A) and dihydromyricetin (FIG. 7B) on preformed α-synuclein fibrils. Samples of aggregated α-synuclein were incubated for 48 hours at 37° C. in the absence or presence of various concentrations of Gn Rb1 or dihydromyricetin (compound: α-synuclein at 6:1, 4:1, and 2:1). The fibril content was then measured by the Th-T binding assay. The assay was performed in triplicate (average of triplicate measurements±standard deviations).

At time 0, the Th-T counts for α-synuclein incubating alone were much higher compared to the Th-T counts of the samples containing Gn Rb1, especially the one containing the highest concentration of the particular ginsenoside. During the course of the experiment, the α-synuclein fibrils that were incubated in the absence of Gn Rb1 continued to aggregate further, as indicated by the increase in Th-T counts, whereas the fibrils incubating in the presence of the ginsenoside disaggregated in a dose-dependent fashion, given the decrease in Th-T counts (FIG. 7A). This trend was apparent after 4 hours of incubation, with the Th-T counts for the Gn Rb1 containing samples being approximately the ⅕ of the Th-T counts of the control.

Figure 7B:
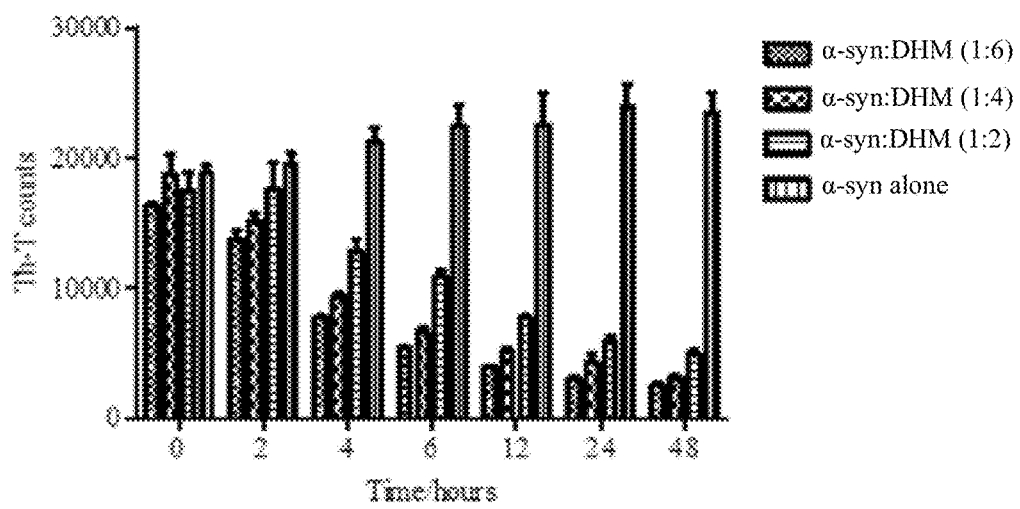

At time 0, the Th-T counts were approximately 20,000 for α-synuclein incubated alone, while in the presence of dihydromyricetin, the Th-T count was less at that time point. The α-synuclein fibrils that were incubated alone continued to aggregate further, as indicated by the increase in Th-T counts, whereas α-synuclein fibrils incubated in the presence of dihydromyricetin disaggregated over time, in a dose dependant fashion, given the decrease in Th-T counts (FIG. 7B). Thus dihydromyricetin disaggregated preformed α-synuclein fibrils in a dose-dependent fashion.

The ability of Gn Rb1 and dihydromyricetin to disaggregate preformed fibrils makes them suitable compounds to be used in the imaging of α-synuclein aggregates such as Lewy bodies, in subjects.

Example 6

The Effect of Salvianolic Acid B and Dihydromyricetin and Gn Rb1 on the Seeding of α-Synuclein Monomers It has been previously shown that the process of amyloid fibril formation follows a nucleation-dependent polymerization model. According to this model, soluble species generate via nucleation oligomeric species (nucleation or lag time phase), which in turn polymerize (polymerization or growth phase) to generate fibrils, thus reaching a final plateau known as the equilibrium phase. Small aggregates or seeds have been shown to accelerate the nucleation phase of amyloid formation in vitro and in vivo via a process known as seeding.

Given that Gn Rb1, salvianolic acid B and dihydromyricetin inhibited α-synuclein fibrillation the effect of Gn Rb1, salvianolic acid B and dihydromyricetin on the seeding of α-synuclein aggregation was determined. Mature α-synuclein fibrils were fragmented by sonication to obtain short fibrils, which were employed as 'seeds'. These short fibrillar seeds were then added to monomeric α-syn, which was allowed to aggregate as described above. The addition of the short fibrillar seeds accelerated the fibrillation process of α-synuclein monomers, as indicated by the increase in Th—S counts.

To assess the effect of salvianolic acid B, dihydromyricetin and Gn Rb1 on the seeding of α-synuclein aggregation, the compounds were added at concentrations of 10 or 50 µM to 100 µM monomeric α-synuclein containing seeds at a final concentration of 2 µM. The mixture was then incubated with continuous mixing at 37° C. for 6 hours.

Figure 8A:
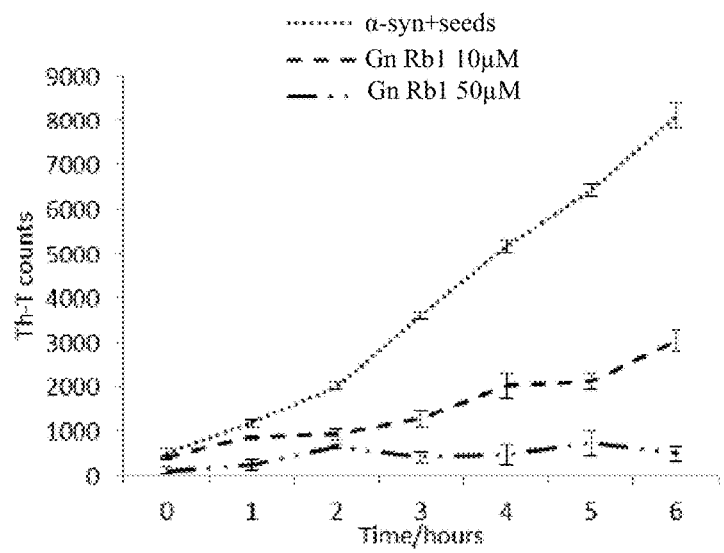
FIGS. 8A-8C show the effect of the compounds Gn Rb1 (FIG. 8A), salvianolic acid B (FIG. 8B) and dihydromyricetin (FIG. 8C) on the seeded polymerisation of α-syn. Samples of α-synuclein monomers (100 µM) were seeded with 2 µM sonicated α-synuclein fibrils, which were incubated in the presence or absence of the compounds at different concentrations (10 and 50 µM) for 6 hours with continuous shaking at 37° C. The extent of fibrillation was estimated by the Th-T binding assay. The assay was performed in triplicate (average of triplicate measurements±standard deviations).
Figure 9A:
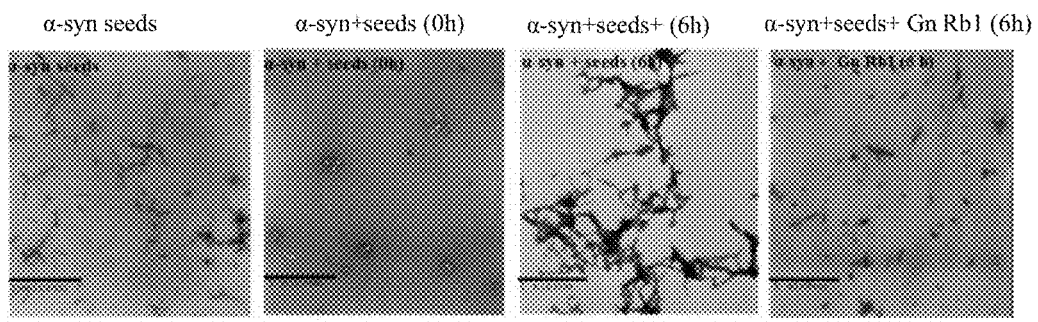
FIGS. 9A-9B show the electron microscopy images of negatively stained samples of the α-synuclein seeds alone and of the seeded α-synuclein incubated in the absence or presence of the compounds 6 hours with continuous shaking at 37° C.

The effect of Gn Rb1 on the seeded aggregation of α-synuclein was apparent after 2 hours of incubation, with the Th-T counts for the control being the double of the counts for the Gn Rb1 containing samples. At this time point, both Gn Rb1 containing samples, which represented two different concentrations of the ginsenoside, gave comparable measurements. However, after 6 hours of incubation the sample containing 50 µM of Gn Rb1 appeared much more efficient than the one containing 10 µM of the Gn Rb1. Indeed, at concentration of 50 µM, Gn Rb1 inhibited the seeding process by approximately 90%, whereas at concentration of 10 µM, it only inhibited the seeding process by approximately 60% (FIG. 8A). These findings were further confirmed by TEM (FIG. 9A). After 6 h of incubation, the seeded α-synuclein formed networks of fibrils, unlike the sample that contained Gn Rb1 that contained mostly globular forms of α-synuclein.

Figure 8B:
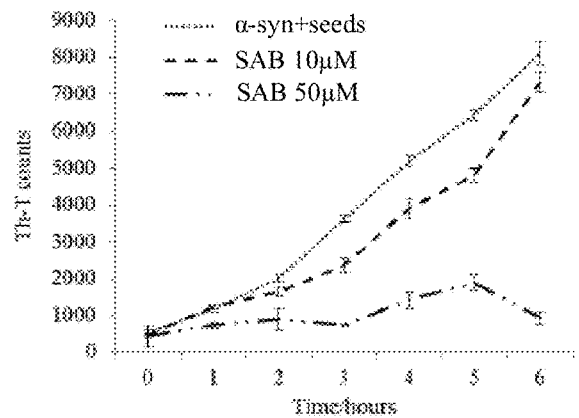
Figure 8C:
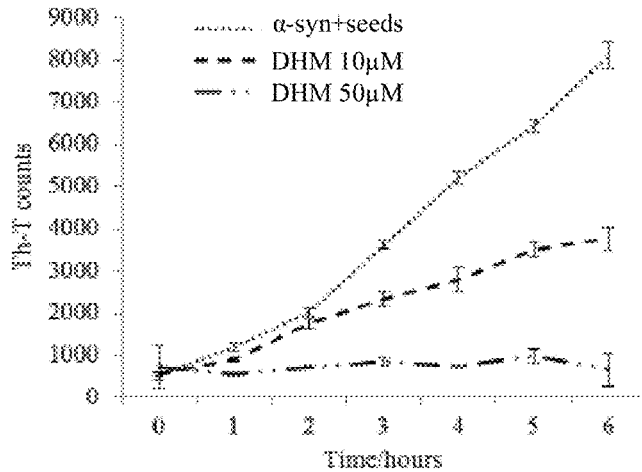
Figure 9B:
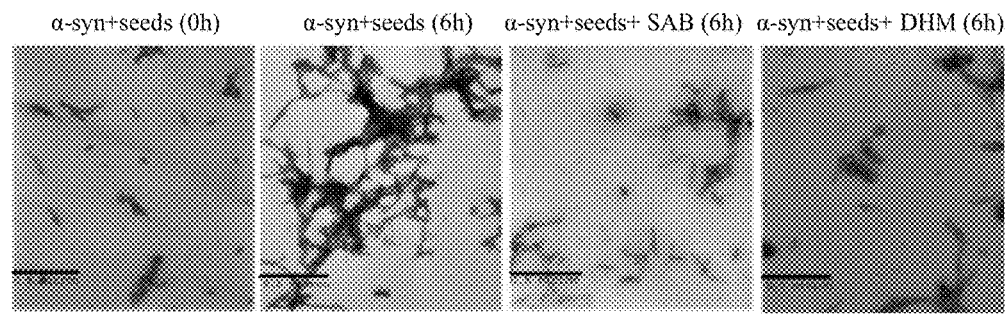

Salvianolic acid B and dihydromyricetin, at a concentration of 50 µM, inhibited the seeding process by approximately 90%, as indicated by the low Th-S counts (FIGS. 8B and 8C). At a lower concentration (10 µM), only dihydromyricetin showed an inhibitory effect on the seeding of α-synuclein monomers, but to a smaller extent in the case of salvianolic acid B. These findings (for 50 µM and 6 hours incubation) were confirmed by TEM (FIG. 9B).

Example 7

Gn Rb1 Inhibition of α-Synuclein Fibrillation is Mediated Via Binding to the Intermediate Species and Forming Stable Oligomers The interaction of Gn Rb1, dihydromyricetin and salvianolic acid B with α-synuclein oligomers was investigated. Monomeric α-synuclein (100 µM) was aggregated in the presence of Gn Rb1 (Gn Rb1:α-synuclein 4:1), dihydromyricetin (DHM: α-synuclein 4:1) or salvianolic acid B (SAB: α-synuclein 4:1). After 5 days of incubation the samples were centrifuged and the supernatant was injected in a superdex 200 SE column.

Figure 10A:
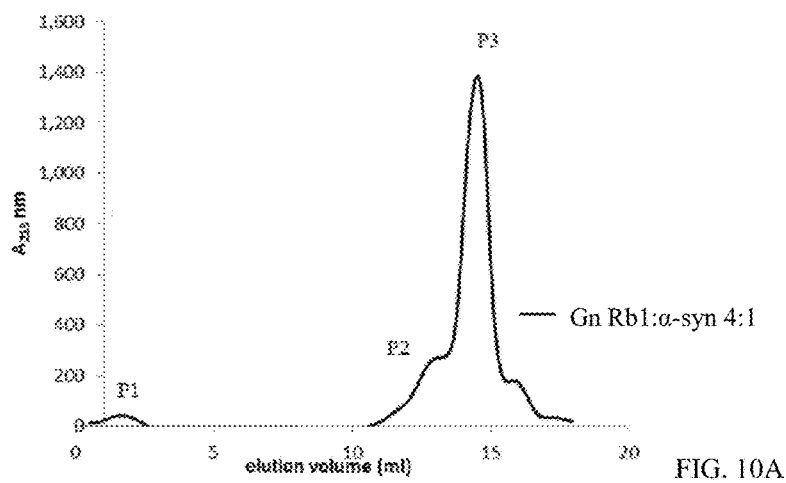
FIGS. 10A-10D show the binding activity of Gn Rb1 to α-synuclein oligomers (Gn Rb1: α-synuclein molar ratio 4:1).

For the Gn Rb1 experiment the elution volume for monomeric α-synuclein was determined by molecular weight standard, and was eluted in a peak corresponding to column volume of 14-16 mL, while oligomeric α-synuclein eluted in a peak corresponding to column volume of approximately 2-3 and 10-14 ml (FIG. 10A).

Figure 11A:
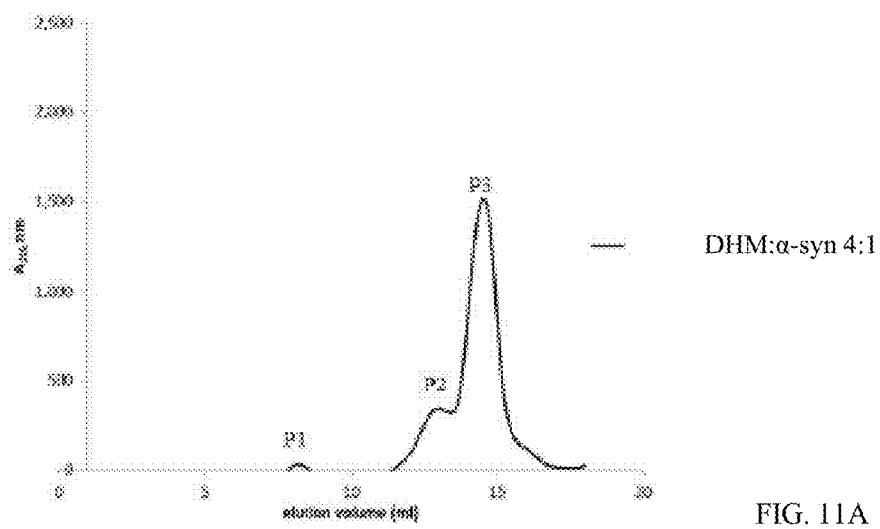
FIGS. 11A-11D show the binding activity of dihydromyricetin to α-synuclein oligomers (DHM: α-syn 4:1).
Figure 12A:
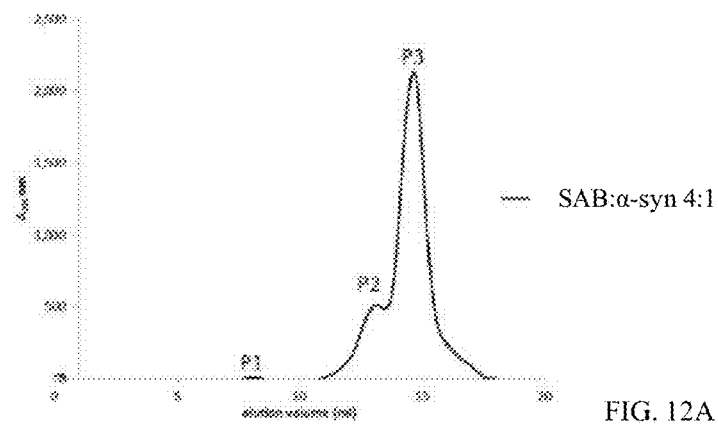
FIGS. 12A-12D show the binding activity of salvianolic acid B to α-syn oligomers (SAB: α-syn 4:1).

For the dihydromyricetin and salvianolic acid B experiments the elution volume for monomeric α-synuclein was determined by molecular weight standard, and was eluted in a peak corresponding to column volume of 14-16 mL (data not shown), while oligomeric α-synuclein eluted in a peak corresponding to column volume of approximately 7-8 and 12-14 ml for P1 and P2 respectively (FIGS. 11A and 12A).

The fractions corresponding to the oligomeric and monomeric α-synuclein peaks were separately pooled together giving rise to P1, P2 and P3 samples, which were concentrated using a speed vac.

The elution was monitored at the absorbance wavelength of 215 nm, immunoblot analysis of the samples P1 P2 and P3 separated by electrophoresis in a 15% SDS-PAGE gel. P1 and P2 samples contain the isolated fractions corresponding to the oligomeric peak and P3 the isolated fractions corresponding to the monomeric peak.

Figure 10B:
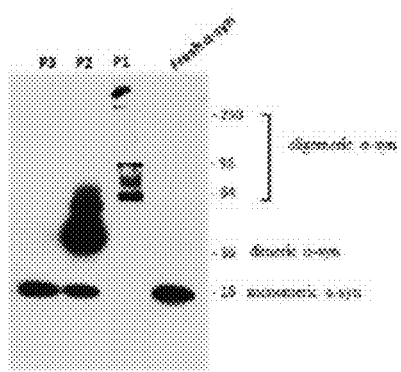
Figure 10C:
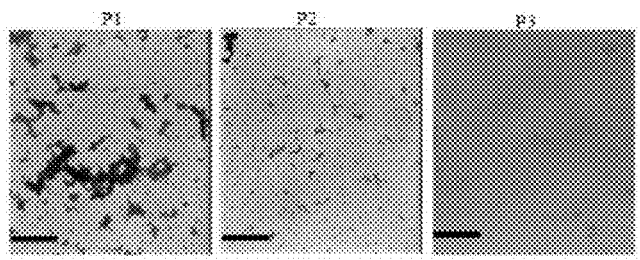
Figure 10:
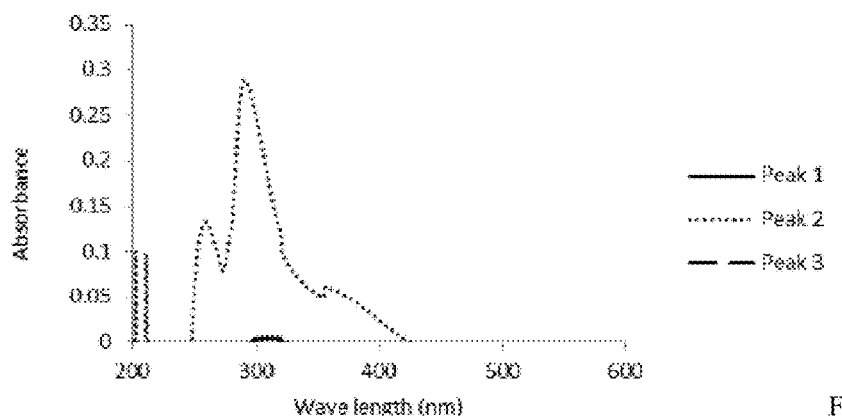
Figure 11B:
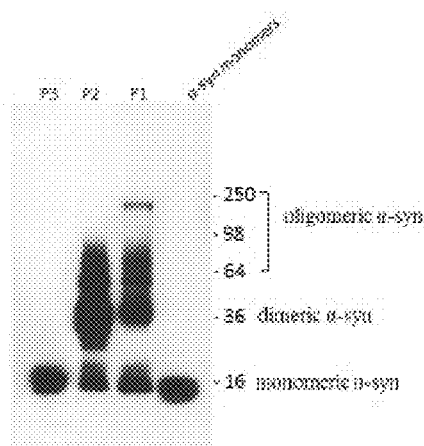
Figure 11C:
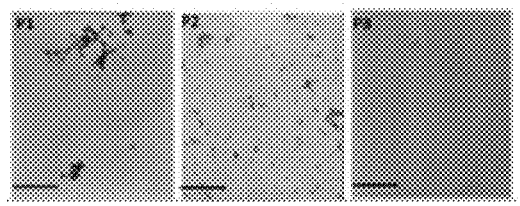
Figure 12B:
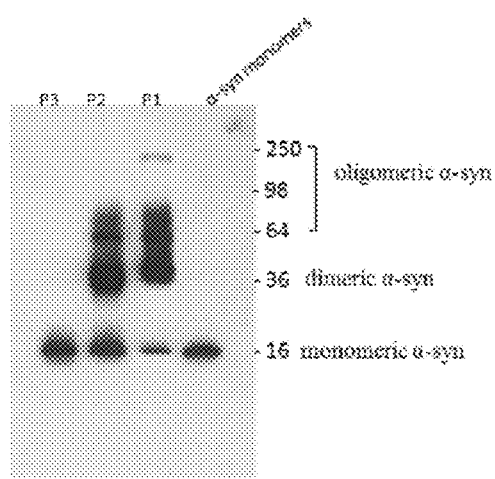
Figure 12C:
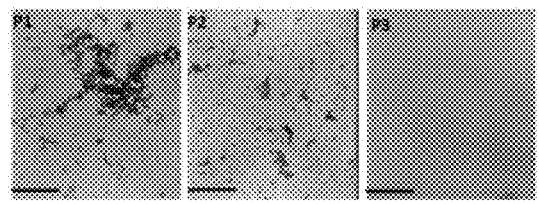

The α-synuclein species in the samples were characterized by western blotting and electron microscopy (FIGS. 10B, C, FIGS. 11B-C, FIGS. 12B-C). Electron microscopy of the same samples indicated the presence of different species of oligomers in P1 and P2 (FIGS. 10C, 11C, 12C), in agreement with the immunoblotting results (FIGS. 10B, 11B, 12B).

To detect the incorporated Gn Rb1 in the P1, P2 and P3 samples, Gn Rb1's ability to produce UV absorbance spectra with three notable peaks was exploited. In the sample containing Gn Rb1: α-synuclein at 4:1 molar ratio, Gn Rb1 was detected only in the oligomeric P2 samples (FIG. 10D).

These results show that Gn Rb1 binds to the oligomeric intermediate species and stabilizes them. To further evaluate whether Gn Rb1 interacts with α-synuclein monomers, a titration of Gn Rb1 into a solution of monomeric α-synuclein was monitored using two-dimensional NMR spectroscopy, which provides signals covering the entire amino acid sequence of α-synuclein. At stoichiometries of up to 6:1 Gn Rb1: α-synuclein no significant chemical shift or resonance intensity changes were observed (FIGS. 13A-D), confirming that Gn Rb1, does not interact significantly with monomeric α-synuclein.

Figure 11D:
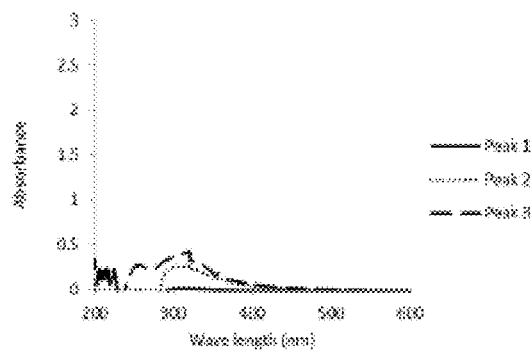

To detect the incorporated dihydromyricetin in the P1, P2 and P3 samples, dihydromyricetin's ability to produce UV absorbance spectra with three notable peaks was exploited. In the sample containing DHM: α-synuclein at 4:1, dihydromyricetin was detected in both P2 and P3 which represent the oligomeric and monomeric species respectively (FIG. 11D).

Figure 12D:
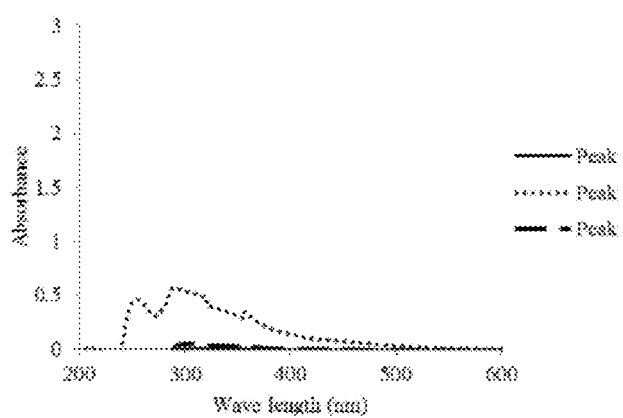
Figure 13A:
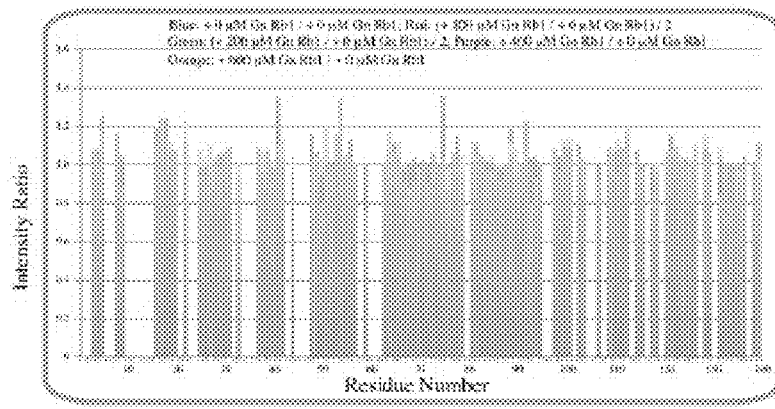
FIGS. 13A-13D show the peak intensity ratio plot of 10004 wildtype α-synuclein FL+Gn Rb1 (Gn Rb1: α-syn 1:1, 4:1 and 6:1).
Figure 13B:
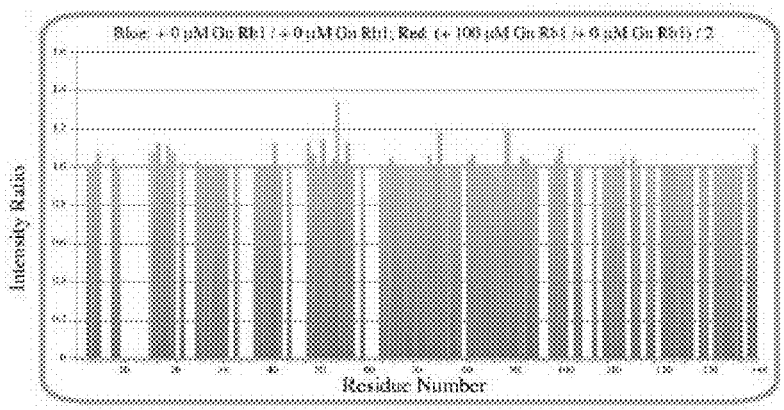
Figure 13C:
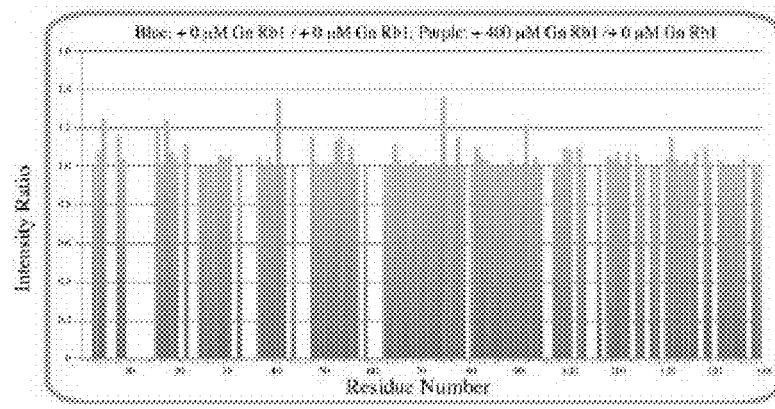
Figure 13D:
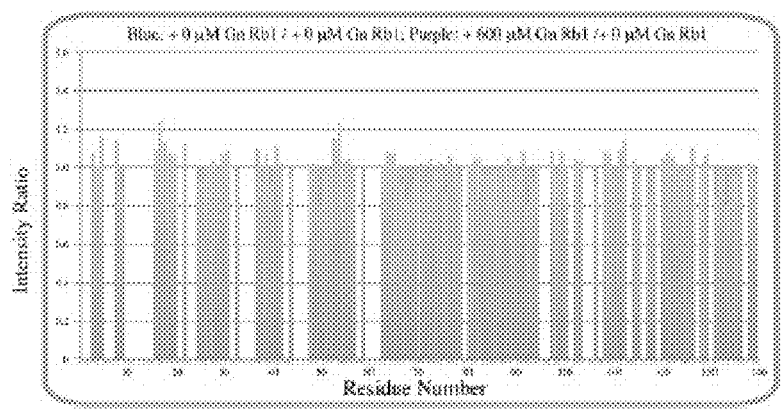

To detect the incorporated salvianolic acid B in the P1, P2 and P3 samples, salvianolic acid B's ability to produce UV absorbance spectra with three notable peaks was exploited. In the sample containing salvianolic acid B: α-synuclein at 4:1, salvianolic acid B was detected in the P2 sample which represents the oligomeric species (FIG. 12D).

These results indicate that the compounds ginsenoside Rb1, dihydromyricetin and salvianolic acid B can bind oligomer forms of α-synuclein and bind and disaggregate preformed fibrils which suggests that these compounds would be suitable for use in the diagnosis of diseases involving α-synuclein and in the imaging of α-synuclein aggregates. The ability of ginsenoside Rb1 and salvianolic acid B to bind oligomeric forms of α-synucleins, but not monomeric forms of α-synuclein, further suggest that Gn Rb1 and salvianolic acid B would be suitable for use in the diagnosis and imaging of aggregates, for disease involving α-synuclein.

These results also indicate that the compounds ginsenoside Rb1, salvianolic acid B and dihydromyricetin provide protection to neuroblastoma cells against α-synuclein toxicity, and can block α-synuclein oligomerisation and fibrillation, thereby suggesting that these compounds would be helpful by removing and/or preventing the formation of α-synuclein aggregates in a subject in the treatment of synucleopathies.

The invention claimed is:

1. A method for detecting α-synuclein aggregates, the method comprising:
   administering ginsenoside Rb1 and a detectable compound to an in vitro sample obtained from a subject, and
   detecting binding of ginsenoside Rb1 to α-synuclein aggregates in the sample by detecting the detectable compound.

2. The method according to claim 1 wherein detecting the binding of ginsenoside Rb1 to α-synuclein aggregates comprises imaging α-synuclein aggregates.

3. The method according to claim 2 wherein the sample is a brain tissue sample.

4. The method according to claim 1 wherein binding of ginsenoside Rb1 to α-synuclein aggregates is detected by autoradiography, positron emission tomography, magnetic resonance imaging, a gamma counter, or a scintillation counter.

5. The method according to claim 1 wherein the α-synuclein aggregates are Lewy bodies, Lewy neurites or cytoplasmic inclusions.

6. The method according to claim 1 wherein the detectable compound is congo red or thioflavin T.

* * * * *